United States Patent
Wen et al.

(10) Patent No.: US 11,998,549 B2
(45) Date of Patent: Jun. 4, 2024

(54) METHODS OF TREATING A VASCULAR LEAKAGE-ASSOCIATED DISEASE OR DISORDER

(71) Applicant: UNITY HEALTH TORONTO, Toronto (CA)

(72) Inventors: Xiao-Yan Wen, Toronto (CA); Anju Philip, Richmond Hill (CA); Claudia Dossantos, Toronto (CA); John Marshall, Toronto (CA)

(73) Assignee: Unity Health Toronto, Toronto (CA)

( * ) Notice: Subject to any disclaimer, the term of this patent is extended or adjusted under 35 U.S.C. 154(b) by 0 days.

(21) Appl. No.: 16/755,008

(22) PCT Filed: Jan. 29, 2020

(86) PCT No.: PCT/CA2020/050106
§ 371 (c)(1),
(2) Date: Apr. 9, 2020

(87) PCT Pub. No.: WO2020/154805
PCT Pub. Date: Aug. 6, 2020

(65) Prior Publication Data
US 2021/0361654 A1   Nov. 25, 2021

Related U.S. Application Data

(60) Provisional application No. 62/797,979, filed on Jan. 29, 2019.

(51) Int. Cl.
*A61K 31/517* (2006.01)
*A61K 31/404* (2006.01)
*A61P 9/00* (2006.01)

(52) U.S. Cl.
CPC .......... *A61K 31/517* (2013.01); *A61K 31/404* (2013.01); *A61P 9/00* (2018.01)

(58) Field of Classification Search
CPC ....... A61K 31/517; A61K 31/404; A61P 9/00; A61P 7/00; A61P 9/14; A61P 29/00; A61P 37/08; A61P 39/00
See application file for complete search history.

(56) References Cited

PUBLICATIONS

El Gazzar, "G9a and HP1 Couple Histone and DNA Methylation to TNFa Transcription Silencing during Endotoxin Tolerance", The Journal of Biological Chemistry, vol. 283, No. 47, pp. 32198-2208, Nov. 21, 2008.*

Singh, "Inhibition of EHMT2 Induces a Robust Antiviral Response Against Foot-and-Mouth Disease and Vesicular Stomatitis Virus Infections in Bovine Cells", Journal of Interferon & Cytokine Research, vol. 36, No. 1 (Year: 2016).*

Alexandraki, I. and Palacio, C. (2010) 'Gram-negative versus Gram-positive bacteremia: what is more alarmin(g)?', Critical Care, 14(3), p. 161. doi: 10.1186/cc9013.

Avdesh, A. et al. (2012) 'Regular care and maintenance of a zebrafish (Danio rerio) laboratory: an introduction.', Journal of visualized experiments□: JoVE, (69), p. e4196. doi: 10.3791/4196.

Cinel, I. and Opal, S. M. (2009) 'Molecular biology of inflammation and sepsis: a primer.', Critical care medicine, 37(1), pp. 291-304. doi: 10.1097/CCM.0b013e31819267fb.

Cole, J. et al. (2016) 'The therapeutic potential of epigenetic manipulation during infectious diseases.', Pharmacology & therapeutics. Elsevier, 167, pp. 85-99. doi: 10.1016/j.pharmthera.2016. 07.013.

Foster, S. L., Hargreaves, D. C. and Medzhitov, R. (2007) 'Gene-specific control of inflammation by TLR-induced chromatin modifications', Nature, 447(7147), pp. 972-978. doi: 10.1038/nature05836.

Fox, E. D. et al. (2013) 'Neutrophils from critically ill septic patients mediate profound loss of endothelial barrier Integrity.', Critical care (London, England). BioMed Central, 17(5), p. R226. doi: 10.1186/cc13049.

Gupta, S. et al. (2018) 'Heat-shock protein-90 prolongs septic neutrophil survival by protecting c-Src kinase and caspase-8 from proteasomal degradation', Journal of Leukocyte Biology, 103(5), pp. 933-944. doi: 10.1002/ JLB.4A0816-354R.

Jiang, L. et al. (2016) 'Alteration of histone H3 lysine 9 dimethylation in peripheral white blood cells of septic patients with trauma and cancer.', Molecular medicine reports. Spandidos Publications, 14(6), pp. 5467-5474. doi: 10.3892/mr.2016.5958.

Marshall, J. C. (2014) 'Why have clinical trials in sepsis failed?', Trends in molecular medicine, 20(4), pp. 195-203. doi: 10.1016/j.molmed.2014.01.007.

(Continued)

*Primary Examiner* — Theodore R. Howell
(74) *Attorney, Agent, or Firm* — BERESKIN & PARR LLP/S.E.N.C.R.L., s.r.l.

(57) ABSTRACT

The present disclosure relates generally to treatment and diagnosis of diseases, disorders or conditions characterized by vascular leakage. More particularly, the present disclosure relates to methods for treating a vascular leakage-associated disease or disorder in a subject; for reducing vascular leakage in a subject; for reducing reactive oxygen species production in a subject; for inducing apoptosis of neutrophils in a subject; and for increasing survival of a subject having a vascular leakage-associated disease or disorder. The methods comprise administering a G9a and/or G9a-like protein (GLP) methyltransferase inhibitor to the subject. The present disclosure further relates to methods for developing a treatment plan for a subject with a vascular leakage-associated disease, disorder or condition, and for identifying a subject as a candidate for treatment of a vascular leakage-associated disease or disorder. The present disclosure relates to use of G9a and/or G9a-like protein (GLP) methyltransferase inhibitor in the treatment of vascular leakage-associated disease, disorder or condition.

11 Claims, 11 Drawing Sheets
Specification includes a Sequence Listing.

(56) References Cited

PUBLICATIONS

Lee, W. L., Ph, D. and Slutsky, A. S. (2010) 'clinical implications of basic research Sepsis and Endothelial Permeability', pp. 689-691.
Nemzek, J. a., Hugunin, K. M. S. and Opp, M. R. (2008) 'Modeling sepsis in the laboratory: Merging sound science with animal well-being', Comparative Medicine, 58(2), pp. 120-128.
Nicodeme, E. et al. (2010) 'Suppression of inflammation by a synthetic histone mimic', Nature, 468(7327), pp. 1119-1123. doi: 10.1038/nature09589.
Philip, A. M. et al. (2017) 'Development of a Zebrafish Sepsis Model for High-Throughput Drug Discovery', Molecular Medicine, 23(1), p. 1. doi: 10.2119/molmed.2016.00188.
Shen, X.-F. et al. (no date) 'Neutrophil dysregulation during sepsis: an overview and update'. doi: 10.1111/ icmm.13112.
Sweis, Ramzi F. et al. Discovery and Development of Potent and Selective Inhibitors of Histone Methyl transferase G9a.ACS Med. Chem. Lett. 2014, 5, 205-209.

\* cited by examiner (A) Control (B) LPS (C) LPS + UNC0642

(D) UNC0642

VE cadherin
Phalloidin - actin
DAPI - nucleus (A)

(B)

METHODS OF TREATING A VASCULAR LEAKAGE-ASSOCIATED DISEASE OR DISORDER

CROSS-REFERENCE TO RELATED APPLICATIONS

The present application is a national phase entry application of Patent Cooperation Treaty Application No. PCT/CA2020/050106, filed Jan. 29, 2020, which claims the benefit of priority from U.S. provisional patent application No. 62/797,979, filed Jan. 29, 2019, the contents of which are incorporated herein by reference in their entirety.

INCORPORATION OF SEQUENCE LISTING

This application includes one or more Sequence Listings pursuant to 37 C.F.R.1.821 et seq., which are disclosed in computer-readable media (file name: 27487-P60286US01_SequenceListing, created on Feb. 21, 2024 and having a size of 751 bytes), which file is herein incorporated by reference in its entirety.

FIELD

The present disclosure relates generally to diseases and disorders characterized by vascular leakage. More particularly, the present disclosure relates to methods of treating and diagnosing a vascular leakage-associated infection and/or inflammation, such as sepsis.

INTRODUCTION

Inflammation is the body's first defense against infection and comprises a series of molecular and cellular mechanisms, and a complex network of controls to keep them in check. Sepsis is characterized by the cardinal signs of inflammation, including vasodilation, heightened cytokine expression, leukocyte diapedesis, increased vascular leakage, and activation of complement and clotting pathways (Medzhitov, 2008). However, these processes occur in tissues that are remote from the infection site, initiating a dysregulated chain of events leading to widespread tissue injury and organ damage (multiple organ dysfunction syndrome (MODS)), which is the cause of the high mortality associated with this disease (Alexandraki and Palacio, 2010). Despite three decades of sepsis research involving mammalian models and over 100 clinical trials, sepsis still affects more than 30 million people worldwide every year, potentially leading to 6 million deaths (WHO 2018). A major health care burden, sepsis, therefore, demands intensive clinical research and radical intervention strategies.

Heretofore, sepsis clinical trials have focused on modifying the host response to sepsis through a number of approaches, including the use of antibiotics against gram negative endotoxin, the use of gamma globulins, monoclonal antibodies against tumor necrosis factor (TNF), blockade of eicosanoid production and interleukin-1 (IL-1) activity, as well as the inhibition of nitric oxide synthase and the administration of activated protein C (John C Marshall, 2014). Yet, these approaches met with modest success in animal experiments and but failed in human clinical trials, leaving no disease modifying drugs for treatment of severe sepsis. The complexity and heterogeneity of the disease (sepsis is believed to alter the expression of over 3714 genes), together with other factors like the timing of intervention, has hindered progress in sepsis research (Nemzek, Hugunin and Opp, 2008; John C Marshall, 2014). Moreover, uses of mouse sepsis disease models and traditional target-based in vitro screens in drug development have many challenges—on average, it takes around 15 years and over 2 billion dollars to develop one drug using these methods.

There is a need for improved methods of treating vascular leakage-associated diseases and disorders, such as sepsis.

SUMMARY

In the present disclosure, it has been demonstrated that G9a and/or G9a-like protein (GLP) methyltransferase inhibitors, and derivatives, salts and/or solvates thereof are able to rescue sepsis-associated phenotypes in animal models, to increase survival rate and decrease vascular leakage in sepsis model animals, to decrease reactive oxygen species (ROS) production and stabilize endothelial monolayer in pulmonary cell models, to decrease pro-inflammatory cytokine levels and increase cellular junction proteins, and to reverse the delay in neutrophil apoptosis observed in sepsis patients. Vascular leakage, increased ROS production, and delayed neutrophil apoptosis are associated with sepsis. It has been demonstrated that G9a and/or GLP methyltransferase inhibitors, derivatives, salts and/or solvates thereof are useful for treating vascular leakage, sepsis and other related diseases, disorders and conditions.

Accordingly, in an aspect of the disclosure, a method of treating a vascular leakage-associated disease, disorder or condition in a subject in need thereof is provided. The method comprises administering an effective amount of a G9a and/or G9a-like protein (GLP) methyltransferase inhibitor to the subject.

In an aspect of the disclosure, a method of reducing vascular leakage in a subject in need thereof is provided. The method comprises administering an effective amount of a G9a and/or GLP methyltransferase inhibitor to the subject.

In an aspect of the disclosure, a method of reducing reactive oxygen species production in a subject in need thereof is provided. The method comprises administering an effective amount of a G9a and/or GLP methyltransferase inhibitor to the subject.

In an aspect of the disclosure, a method of inducing apoptosis of neutrophils in a subject in need thereof is provided. The method comprises administering an effective amount of a G9a and/or GLP methyltransferase inhibitor to the subject.

In an aspect of the disclosure, a method of increasing survival of a subject having a vascular leakage-associated disease, disorder or condition is provided. The method comprises administering an effective amount of a G9a and/or GLP methyltransferase inhibitor to the subject.

In an aspect of the disclosure, a method of developing a treatment plan for a subject with a vascular leakage-associated disease, disorder or condition is provided. The method comprises assaying a sample obtained from the subject for a level or activity of G9a and/or GLP methyltransferase, comparing to a level or activity of G9a and/or GLP methyltransferase in a control sample, and selecting a G9a and/or GLP methyltransferase inhibitor for administration to the subject if the level or activity of the G9a and/or GLP methyltransferase in the sample obtained from the subject is increased as compared to the level or activity of G9a and/or G9a-like protein (GLP) methyltransferase of the control sample.

In an aspect of the disclosure, a method of developing a treatment plan for a subject with a vascular leakage-associated disease, disorder or condition is provided. The method comprises assaying a sample obtained from the subject for a level or activity of G9a and/or GLP methyltransferase, comparing to a level or activity of G9a and/or GLP methyltransferase in a control sample and administering a G9a and/or GLP methyltransferase inhibitor to the subject if the level or activity of the G9a and/or GLP methyltransferase in the sample obtained from the subject is increased as compared to the level or activity of G9a and/or G9a-like protein (GLP) methyltransferase of the control sample.

In an aspect of the disclosure, a method of identifying a subject as a candidate for treatment of a vascular leakage-associated disease, disorder or condition with a G9a and/or GLP methyltransferase inhibitor is provided. The method comprises assaying a sample obtained from the subject for a level or activity of G9a and/or GLP methyltransferase, comparing to a level or activity of G9a and/or GLP methyltransferase in a control sample, and identifying the subject as a candidate for treatment of the vascular leakage-associated disease or disorder with the G9a and/or GLP methyltransferase inhibitor if the level or activity of the G9a and/or GLP methyltransferase in the sample obtained from the subject is increased as compared to the level or activity of the G9a and/or GLP methyltransferase of the control sample.

In an aspect, the present disclosure includes a use of a G9a and/or G9a-like protein methyltransferase inhibitor in the treatment of a vascular leakage-associated disease, disorder or condition.

In an aspect, the present disclosure includes a use of a G9a and/or G9a-like protein methyltransferase inhibitor in the manufacture of a medicament for the treating a vascular leakage-associated disease, disorder or condition.

In an aspect, the present disclosure includes a use of a G9a and/or G9a-like protein methyltransferase inhibitor in the reduction of vascular leakage.

In an aspect, the present disclosure includes a use of a G9a and/or G9a-like protein methyltransferase inhibitor in the manufacture of a medicament for reducing vascular leakage.

In an aspect, the present disclosure includes a use of a G9a and/or G9a-like protein methyltransferase inhibitor in the reduction of reactive oxygen species.

In an embodiment, the reactive oxygen species production is associated with infection, inflammation and/or endothelial damage.

In an embodiment, the reactive oxygen species production is associated with sepsis.

In an embodiment, the reactive oxygen species production occurs in the vascular system.

In an embodiment, the reactive oxygen species are produced by immune cells.

In an aspect, the present disclosure includes a use of a G9a and/or G9a-like protein methyltransferase inhibitor in the manufacture of a medicament for reducing reactive oxygen species.

In an aspect, the present disclosure includes a use of a G9a and/or G9a-like protein methyltransferase inhibitor in the induction of neutrophil apoptosis.

In an embodiment, the subject has an increased number of neutrophils associated with infection and/or inflammation.

In an embodiment, the subject has an increased number of neutrophils associated with sepsis.

In an embodiment, the neutrophils undergo apoptosis induced by the G9a and/or GLP methyltransferase inhibitor.

In an aspect, the present disclosure includes a use of a G9a and/or G9a-like protein methyltransferase inhibitor in the manufacture of a medicament for inducing neutrophil apoptosis.

In an aspect, the present disclosure includes a use of a G9a and/or G9a-like protein methyltransferase inhibitor in the increase of survival of a subject having a vascular leakage-associated disease, disorder or condition.

In an aspect, the present disclosure includes a use of a G9a and/or G9a-like protein methyltransferase inhibitor in the manufacture of a medicament for increasing survival of a subject having a vascular leakage-associated disease, disorder or condition.

In an embodiment, the G9a and/or G9a-like protein methyltransferase inhibitor is for intravenous, intramuscular, oral buccal, nasal, rectal, subcutaneous use, or a combination thereof.

In an embodiment, the vascular leakage-associated disease, disorder or condition is an infection and/or inflammation.

In an embodiment, the vascular leakage-associated disease, disorder or condition is selected from sepsis, acute respiratory distress syndrome (ARDS), influenza virus infection, SARS virus infection, MERS-CoV virus infection, 2019-nCoV virus infection, Dengue virus infection, Ebola virus infection, pancreatitis, trauma, post-transplant ischemia-reperfusion injury, and combinations thereof.

In an embodiment of, the vascular leakage-associated disease, disorder or condition is sepsis.

In an embodiment, the subject is a mammal.

In an embodiment, the subject is a human.

In an embodiment of, the administering of the G9a and/or GLP methyltransferase inhibitor is by a route selected from intravenous, intramuscular, oral, buccal, nasal, rectal, subcutaneous route of administration; and a combination thereof.

In an embodiment, the G9a and/or GLP methyltransferase inhibitor is selected from A366, UNC0638 or UNC0642, a derivative thereof, a pharmaceutically acceptable salt and/or solvate thereof, and combinations thereof.

Other features and advantages of the disclosure will become more apparent from the following detailed description and from the exemplary embodiments.

DRAWINGS

The embodiments of the application will now be described in greater detail with reference to the attached drawings in which:

FIG. 1 shows data indicating that UNC0642 rescues sepsis-associated phenotypes in a zebrafish model of sepsis. Panel A shows % survival of zebrafish sepsis model treated with various doses of UNC0642. Panels B, C, and D show edema and tail swelling, vascular leakage and ROS production respectively in LPS-treated zebrafish treated with or without UNC0642.

FIG. 2 shows data indicating that UNC0642 offers protection against sepsis-associated mortality and protein leakage in a mouse cecal ligation and puncture (CLP) model of sepsis. Panel A shows % survival of treated and untreated sham and CLP animals with time. Panel B shows protein leakage for treated and untreated sham and CLP animals.

FIG. 3 shows data indicating that UNC0642 stabilizes the endothelial monolayer and mitigates lipopolysaccharide (LPS) induced vascular leakage in cultured human pulmonary microvascular endothelial cells (HPMECs); UNC0642 also rescues TNFα-induced reactive oxygen species (ROS) production in beas2b airway epithelial cells. Panel A shows FITC dextran fluorescence assay in HPMEC. Panel B shows dichlorofluoroscein (DCF) assay for measuring ROS level in TNFα-treated beas2b airway epithelial cells with or without UNC0642.

Figure 1:
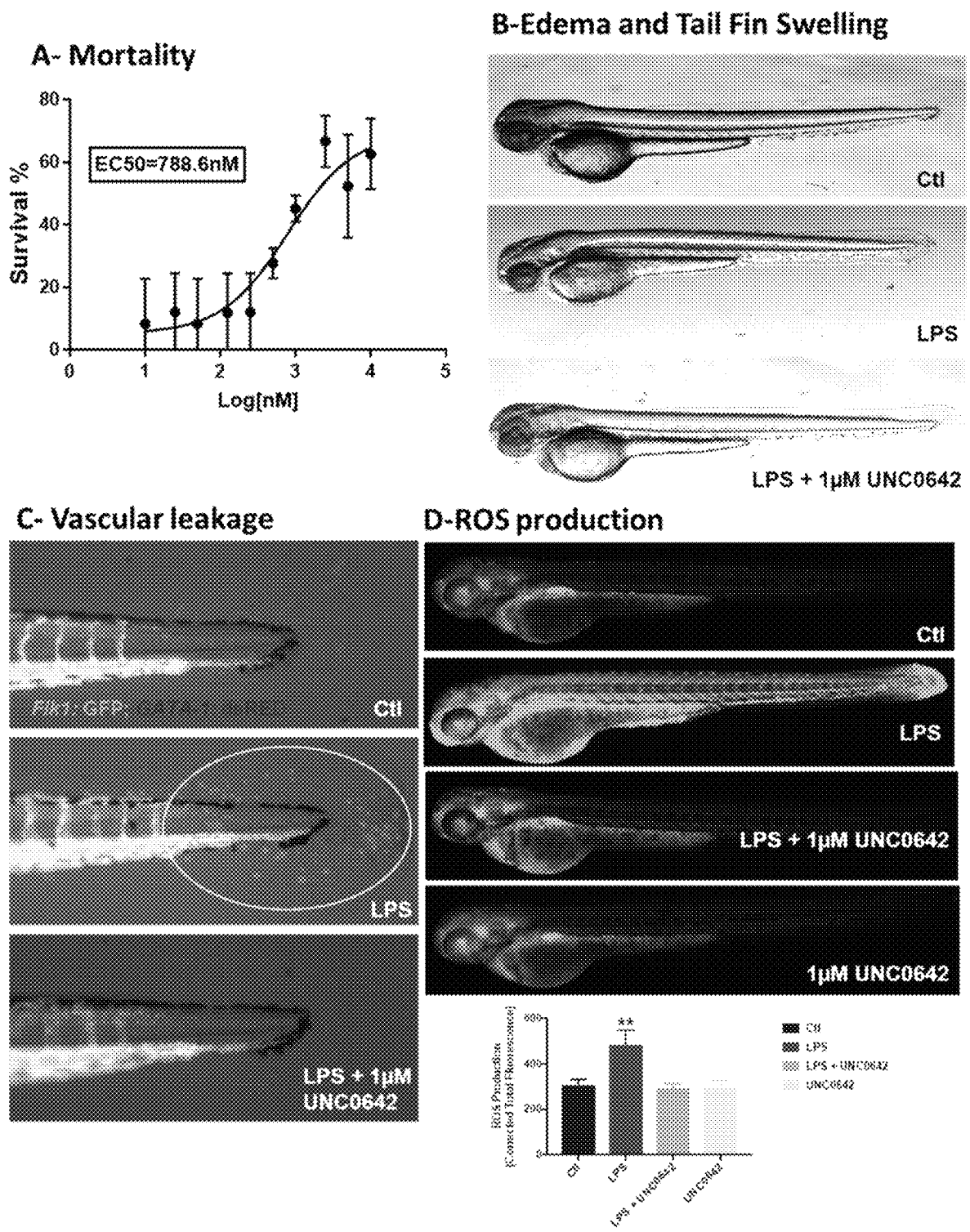
Figure 2:
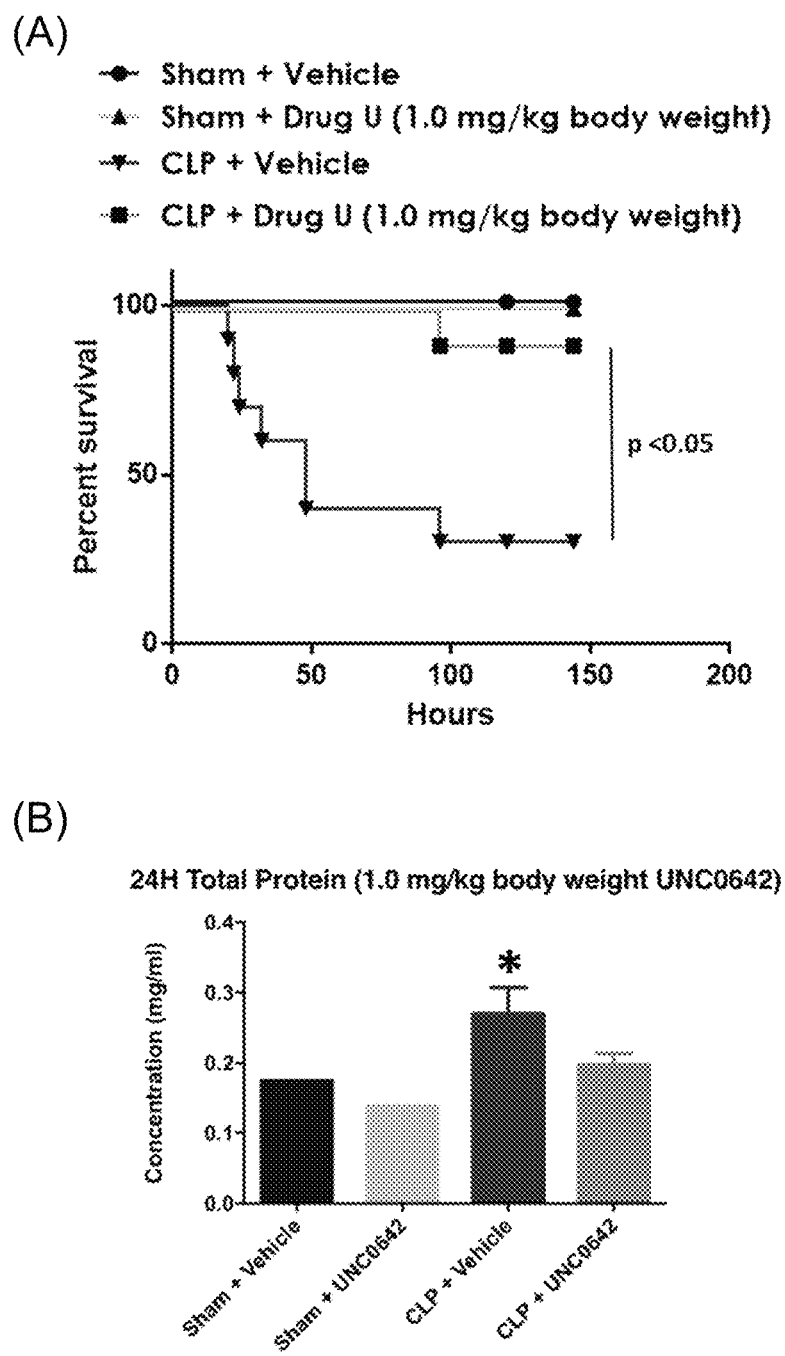
Figure 3:
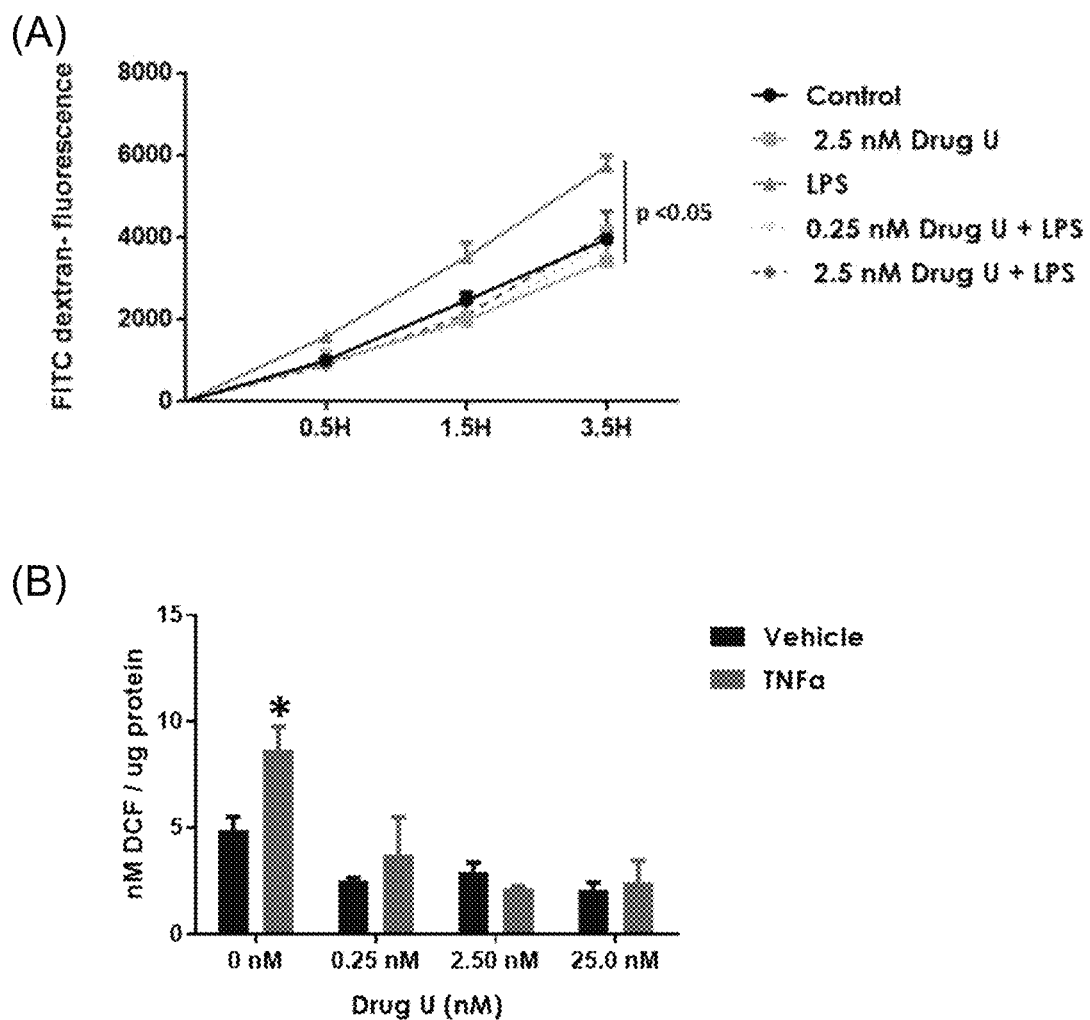
Figure 4:
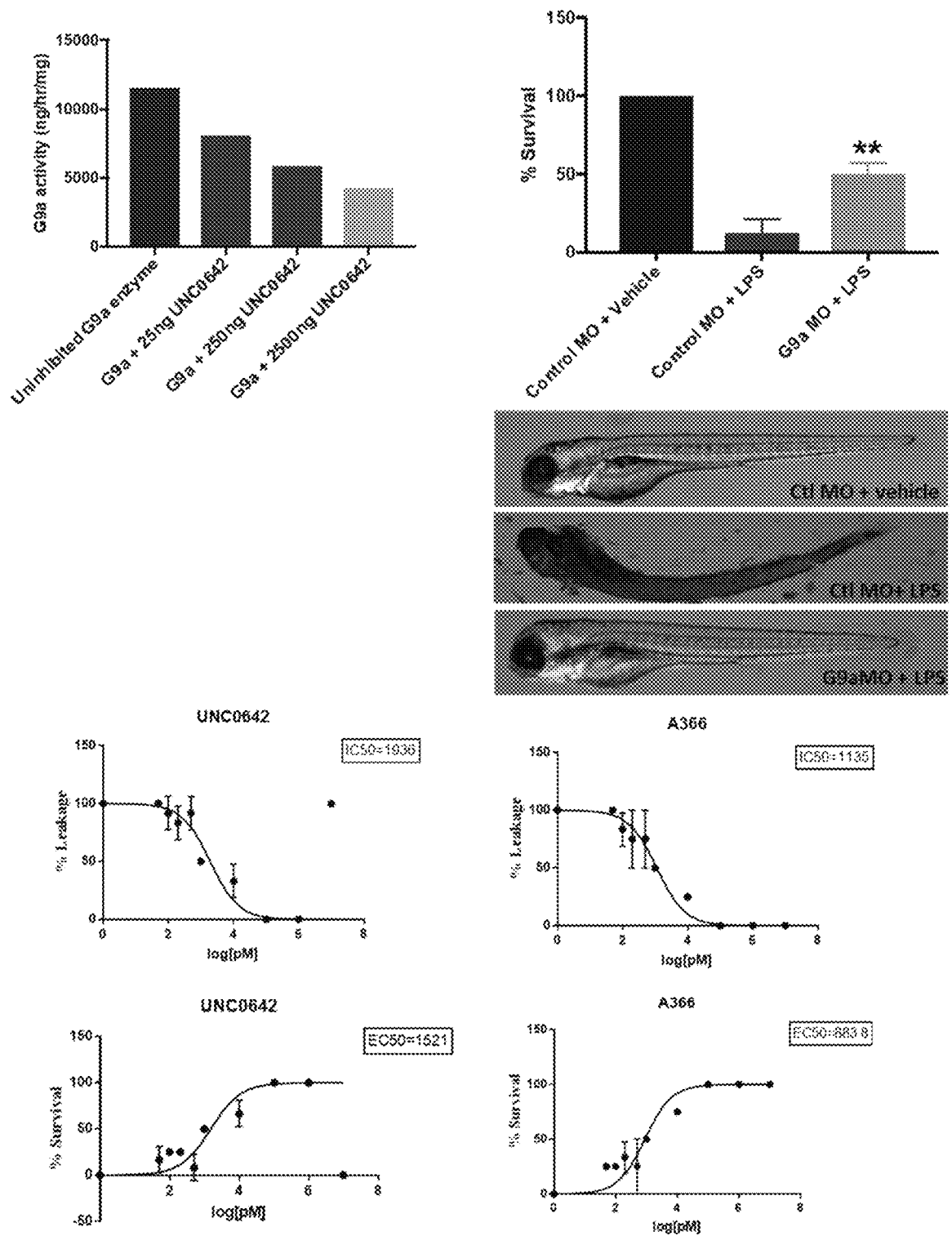
FIG. 4 shows validation data of drug target G9a methyltransferase.
Figure 5:
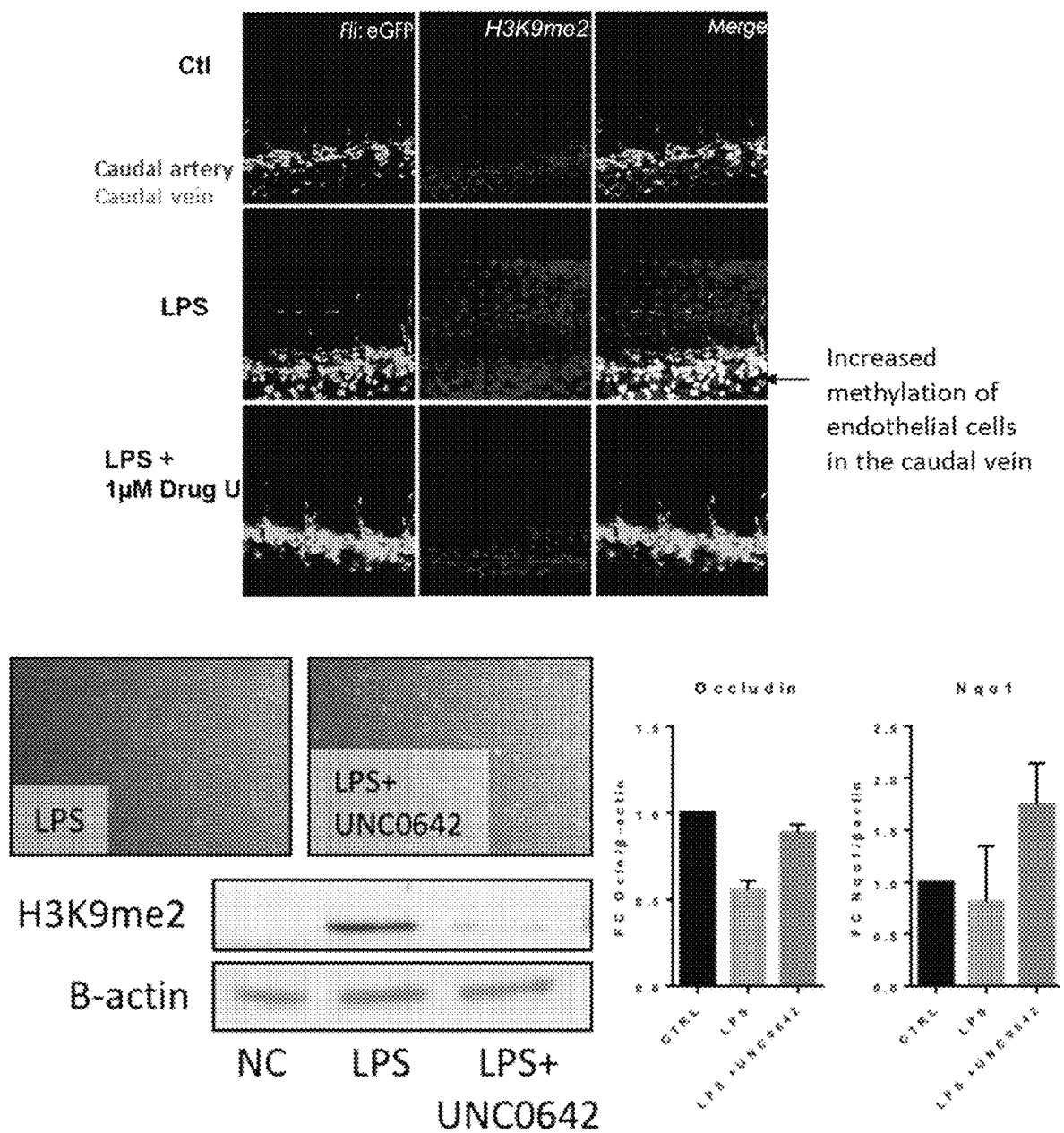
FIG. 5 shows data indicating that UNC0642 alters LPS-induced histone H3 lysine 9 dimethylation (H3K9me2) in zebrafish endothelial cells and HPMECs with parallel changes in cell junction and antioxidant proteins.
Figure 6:
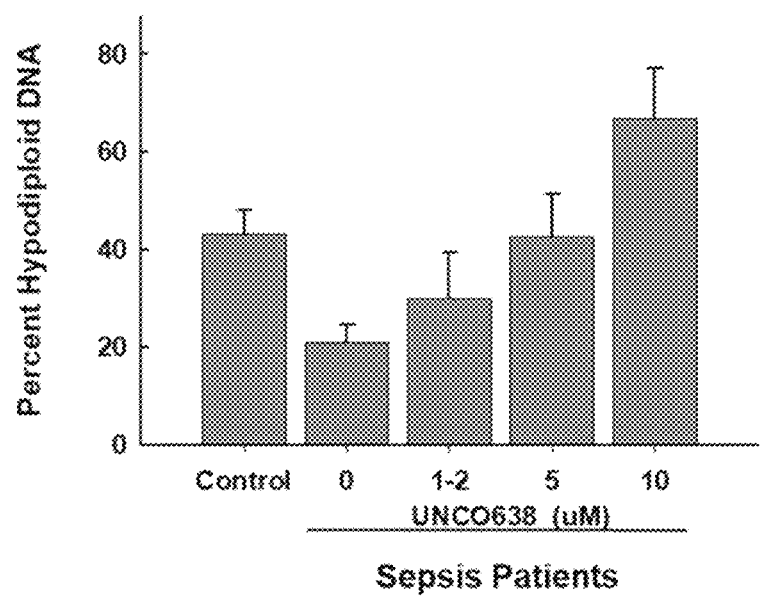
FIG. 6 shows data indicating that G9a methyltransferase inhibitor reverses the delay in neutrophil apoptosis seen in sepsis patients.

Other features and advantages of the disclosure will become more apparent from the following detailed description and from the exemplary embodiments.

DESCRIPTION OF VARIOUS EMBODIMENTS

Methods for treating a vascular leakage-associated disease, disorder or condition in a subject; for reducing vascular leakage in a subject; for reducing reactive oxygen species production in a subject; for inducing apoptosis of neutrophils in a subject; for increasing survival of a subject having a vascular leakage-associated disease, disorder or condition; for developing a treatment plan for a subject with a vascular leakage-associated disease, disorder or condition; and for identifying a subject as a candidate for treatment of a vascular leakage-associated disease, disorder or condition with a G9a and/or GLP methyltransferase inhibitor are disclosed. Uses of a G9a and/or GLP methyltransferase inhibitor in the treatment of a vascular leakage-associated diseases, in the reduction of vascular leakage, in the reduction of reactive oxygen species, in the induction of neutrophil apoptosis, and in the increase of survival of a subject having a vascular leakage-associated disease, disorder or condition are provided. Uses of a G9a and/or GLP methyltransferase inhibitor in the manufacture of medicament are also provided.

Accordingly, in an aspect of the disclosure, a method of treating a vascular leakage-associated disease, disorder or condition in a subject in need thereof is provided. The method comprises administering an effective amount of a G9a and/or G9a-like protein (GLP) methyltransferase inhibitor to the subject.

In an aspect of the disclosure, a method of reducing vascular leakage in a subject in need thereof is provided. The method comprises administering an effective amount of a G9a and/or GLP methyltransferase inhibitor to the subject.

In an aspect of the disclosure, a method of reducing reactive oxygen species production in a subject in need thereof is provided. The method comprises administering an effective amount of a G9a and/or GLP methyltransferase inhibitor to the subject.

In an aspect of the disclosure, a method of inducing apoptosis of neutrophils in a subject in need thereof is provided. The method comprises administering an effective amount of a G9a and/or GLP methyltransferase inhibitor to the subject.

In an aspect of the disclosure, a method of increasing survival of a subject having a vascular leakage-associated disease, disorder or condition is provided. The method comprises administering an effective amount of a G9a and/or GLP methyltransferase inhibitor to the subject.

In an aspect of the disclosure, a method of developing a treatment plan for a subject with a vascular leakage-associated disease, disorder or condition is provided. The method comprises assaying a sample obtained from the subject for a level or activity of G9a and/or GLP methyltransferase, comparing to a level or activity of G9a and/or GLP methyltransferase in a control sample, and selecting a G9a and/or GLP methyltransferase inhibitor for administration to the subject if the level or activity of the G9a and/or GLP methyltransferase in the sample obtained from the subject is increased as compared to the level or activity of G9a and/or G9a-like protein (GLP) methyltransferase of the control sample.

In an aspect of the disclosure, a method of developing a treatment plan for a subject with a vascular leakage-associated disease, disorder or condition is provided. The method comprises assaying a sample obtained from the subject for a level or activity of G9a and/or GLP methyltransferase, comparing to a level or activity of G9a and/or GLP methyltransferase in a control sample and administering a G9a and/or GLP methyltransferase inhibitor to the subject if the level or activity of the G9a and/or GLP methyltransferase in the sample obtained from the subject is increased as compared to the level or activity of G9a and/or G9a-like protein (GLP) methyltransferase of the control sample.

In an aspect of the disclosure, a method of identifying a subject as a candidate for treatment of a vascular leakage-associated disease, disorder or condition with a G9a and/or GLP methyltransferase inhibitor is provided. The method comprises assaying a sample obtained from the subject for a level or activity of G9a and/or GLP methyltransferase, comparing to a level or activity of G9a and/or GLP methyltransferase in a control sample, and identifying the subject as a candidate for treatment of the vascular leakage-associated disease or disorder with the G9a and/or GLP methyltransferase inhibitor if the level or activity of the G9a and/or GLP methyltransferase in the sample obtained from the subject is increased as compared to the level or activity of the G9a and/or GLP methyltransferase of the control sample.

In an aspect, the present disclosure includes a use of a G9a and/or G9a-like protein methyltransferase inhibitor in the treatment of a vascular leakage-associated disease, disorder or condition.

In an aspect, the present disclosure includes a use of a G9a and/or G9a-like protein methyltransferase inhibitor in the manufacture of a medicament for the treating a vascular leakage-associated disease, disorder or condition.

In an aspect, the present disclosure includes a use of a G9a and/or G9a-like protein methyltransferase inhibitor in the reduction of vascular leakage.

In an aspect, the present disclosure includes a use of a G9a and/or G9a-like protein methyltransferase inhibitor in the manufacture of a medicament for reducing vascular leakage.

In an aspect, the present disclosure includes a use of a G9a and/or G9a-like protein methyltransferase inhibitor in the reduction of reactive oxygen species.

In an embodiment, the reactive oxygen species production is associated with infection, inflammation and/or endothelial damage.

In an embodiment, the reactive oxygen species production is associated with sepsis.

In an embodiment, the reactive oxygen species production occurs in the vascular system.

In an embodiment, the reactive oxygen species are produced by immune cells.

In an aspect, the present disclosure includes a use of a G9a and/or G9a-like protein methyltransferase inhibitor in the manufacture of a medicament for reducing reactive oxygen species.

In an aspect, the present disclosure includes a use of a G9a and/or G9a-like protein methyltransferase inhibitor in the induction of neutrophil apoptosis.

In an embodiment, the subject has an increased number of neutrophils associated with infection and/or inflammation.

In an embodiment, the subject has an increased number of neutrophils associated with sepsis.

In an embodiment, the neutrophils undergo apoptosis induced by the G9a and/or GLP methyltransferase inhibitor.

In an aspect, the present disclosure includes a use of a G9a and/or G9a-like protein methyltransferase inhibitor in the manufacture of a medicament for inducing neutrophil apoptosis.

In an aspect, the present disclosure includes a use of a G9a and/or G9a-like protein methyltransferase inhibitor in the increase of survival of a subject having a vascular leakage-associated disease, disorder or condition.

In an aspect, the present disclosure includes a use of a G9a and/or G9a-like protein methyltransferase inhibitor in the manufacture of a medicament for increasing survival of a subject having a vascular leakage-associated disease, disorder or condition.

In an embodiment, the G9a and/or G9a-like protein methyltransferase inhibitor is for intravenous, intramuscular, oral buccal, nasal, rectal, subcutaneous use, or a combination thereof.

In an embodiment, the vascular leakage-associated disease, disorder or condition is an infection and/or inflammation.

In an embodiment, the vascular leakage-associated disease, disorder or condition is selected from sepsis, acute respiratory distress syndrome (ARDS), influenza virus infection, SARS virus infection, MERS-CoV virus infection, 2019-nCoV virus infection, Dengue virus infection, Ebola virus infection, pancreatitis, trauma, post-transplant ischemia-reperfusion injury, and combinations thereof.

In an embodiment of, the vascular leakage-associated disease, disorder or condition is sepsis.

In an embodiment, the subject is a mammal.

In an embodiment, the subject is a human.

In an embodiment of, the administering of the G9a and/or GLP methyltransferase inhibitor is by a route selected from intravenous, intramuscular, oral, buccal, nasal, rectal, subcutaneous route of administration; and a combination thereof.

In an embodiment, the G9a and/or GLP methyltransferase inhibitor is selected from A366, UNC0638 or UNC0642, a derivative thereof, a pharmaceutically acceptable salt and/or solvate thereof, and combinations thereof.

Definitions

The terminology used herein is for the purpose of describing particular embodiments only and is not intended to be limiting of example embodiments of the invention. Unless defined otherwise, all technical and scientific terms used herein generally have the same meaning as commonly understood by one of ordinary skill in the art to which this disclosure belongs.

As used herein, the singular forms "a," "an," and "the," are intended to include the plural forms as well, unless the context clearly indicates otherwise.

The phrase "and/or" should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, the phrase "one or more," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "one or more" refers, whether related or unrelated to those elements specifically identified. Thus, as a non-limiting example, "one or more of A and B" (or, equivalently, "one or more of A or B," or, equivalently "one or more of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In embodiments comprising an "additional" or "second" component, such as an additional or second compound, the second component as used herein is chemically different from the other components or first component. A "third" component is different from the other, first, and second components, and further enumerated or "additional" components are similarly different.

When the term "about", "substantially" and "approximately" as used herein in conjunction with a numerical range, it modifies that range by extending the boundaries above and below those numerical values. In general, the term "about" is used herein to modify a numerical value above and below the stated value by a variance of 20%, 10%, 5%, or 1% if this deviation would not negate the meaning of the word it modifies or unless the context suggests otherwise to a person skilled in the art. In certain embodiments, the term "about" is used to modify a numerical value above and below the stated value by a variance of 10%. In certain embodiments, the term "about" is used to modify a numerical value above and below the stated value by a variance of 5%. In certain embodiments, the term "about" is used to modify a numerical value above and below the stated value by a variance of 1%.

When a range of values is listed herein, it is intended to encompass each value and sub-range within that range. For example, "1-5 ng" is intended to encompass 1 ng, 2 ng, 3 ng, 4 ng, 5 ng, 1-2 ng, 1-3 ng, 1-4 ng, 1-5 ng, 2-3 ng, 2-4 ng, 2-5 ng, 3-4 ng, 3-5 ng, and 4-5 ng.

A "subject" as used herein includes all members of the animal kingdom, including a mammal (e.g., a non-human mammal), including a primate and a human. Mammals include, but are not limited to, primates, humans, farm animals, sport animals, and pets.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

The term "treatment", "treat" or "treating" or "amelioration" as used herein is an approach for obtaining beneficial or desired clinical results. For purposes of this disclosure, beneficial or desired clinical results include, but are not limited to, one or more of the following: reduction in inflammation, decreased extent of damage from a disease, condition, or disorder, decreased duration of a disease, condition, or disorder, and/or reduction in the number, extent, or duration of symptoms related to a disease, condition, or disorder. The term includes the administration of the compounds, agents, drugs or pharmaceutical compositions of the present disclosure to prevent or delay the onset of one or more symptoms, complications, or biochemical indicia of a disease or condition; lessening or improving one or more symptoms; shortening or reduction in duration of a symptom; or arresting or inhibiting further development of a disease, condition, or disorder. Treatment may be prophylactic (to prevent or delay the onset of a disease, condition, or disorder, or to prevent the manifestation of clinical or subclinical symptoms thereof) or therapeutic suppression or alleviation of symptoms after the manifestation of the disease, condition, or disorder.

The term "vascular leakage" as used herein refers to a condition where at least a part of the vascular system, such as a blood vessel, allows for passage of at least a blood cell through a layer of endothelial cells forming the wall of the blood vessel. Vascular leakage may encompass, for example, vascular permeability, microvascular permeability, or capillary permeability. Methods for assessing the presence and/or measuring the extent of vascular leakage include, but are not limited to transwell permeability assays, trans endothelial electrical resistance (TEER) measurements and lung permeability assays. Vascular leakage may be associated with a number of diseases or disorders, as known to one of ordinary skill in the art.

The term "vascular leakage-associated disease or disorder" as used herein refers to a disease, disorder, or condition in which at least one symptom is vascular leakage. In a vascular leakage-associated disease or disorder, the cause of the vascular leakage may be inflammation. Examples of inflammation that may lead to vascular leakage include, but are not limited to, inflammation due to infection, inflammation due to acute respiratory distress syndrome (ARDS), inflammation due to pancreatitis, inflammation due to physical trauma or injury, inflammation due to surgery, or inflammation due to post-transplant ischemia-reperfusion injury. A vascular leakage-associated disease or disorder may be an infection. The infection may be a primary or an opportunistic infection, and may be of viral, bacterial, fungal, or parasitic origin. In embodiments of the disclosure, the infection is sepsis (of bacterial, viral, or other origin), influenza virus infection, SARS virus infection, MERS-CoV virus infection, 2019-nCoV virus infection, Dengue virus infection, or Ebola virus infection. In a preferred embodiment of the disclosure, the vascular leakage-associated disease or disorder is sepsis.

The term "neutrophil" refers to a type of immune cell in the blood stream or at a site of infection or inflammation. Neutrophils may also be referred to, for example, as granulocytes or polymorphonuclear cells (PMN). Neutrophils may produce ROS as part of the inflammatory response to a vascular leakage-associated disease or disorder. The number of neutrophils in a subject may also be increased in a vascular leakage-associated disease or disorder, such as sepsis. Disclosed herein are methods for increasing apoptosis (programmed cell death) of neutrophils in a subject with a vascular leakage-associated disease or disorder.

The term "administering," refers to the placement of an agent, a drug, a compound, or a pharmaceutical composition as disclosed herein into a subject by a method or route which results in at least partial delivery of the composition at a desired site. The agent, drug, compound, or pharmaceutical composition disclosed herein can be administered by any appropriate route which results in an effective treatment in the subject. Examples of administering may include, but are not limited to, intravenous, intramuscular, oral, buccal, nasal, rectal, or subcutaneous routes of administration.

The term "effective amount" as used herein is an amount sufficient to affect any one or more beneficial or desired results. In more specific aspects, an effective amount may prevent, alleviate or ameliorate symptoms of a disease, condition, or disorder. For prophylactic use, beneficial or desired results may include eliminating or reducing the risk, lessening the severity, or delaying the onset of a disease, condition, or disorder, including biochemical, histological and/or behavioral symptoms of the disease, condition, or disorder, its complications and intermediate pathological phenotypes presenting during development of the disease, condition, or disorder. For therapeutic use, beneficial or desired results may include clinical results such as reducing one or more symptoms of a vascular leakage-associated disease, decreasing the dose of other medications required to treat the disease, enhancing the effect of another medication, and/or delaying the progression of the disease in a subject. Beneficial or desired results may also include reducing vascular leakage in a subject, reducing reactive oxygen species production in a subject, inducing apoptosis of neutrophils in a subject, or increasing survival of a subject having a vascular leakage-associated disease. An effective dosage can be administered in one or more administrations.

For purposes of this disclosure, an effective dosage of an agent, a drug, a compound, or a pharmaceutical composition is an amount sufficient to accomplish therapeutic or prophylactic treatment either directly or indirectly. As is understood in the clinical context, an effective dosage of an agent, a drug, a compound, or a pharmaceutical composition may or may not be achieved in conjunction with another agent, drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved. The amount may vary from one subject to another and may depend upon one or more factors, such as, for example, subject gender, age, body weight, subject's health history, and/or the underlying cause of the disease, condition, or disorder to be prevented, inhibited and/or treated.

The term "pharmaceutically acceptable carrier" or "pharmaceutically acceptable excipient" as used herein includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. In some embodiments, diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, P A, 1990; and Remington, The Science and Practice of Pharmacy 20th Ed. Mack Publishing, 2000).

The term "pharmaceutically acceptable salt" means either an acid addition salt or a base addition salt, which is suitable for, or compatible with, the treatment of subjects.

An acid addition salt suitable for, or compatible with, the treatment of subjects is any non-toxic organic or inorganic acid addition salt of any basic compound.

A base addition salt suitable for, or compatible with, the treatment of subjects is any non-toxic organic or inorganic base addition salt of any acidic compound.

The term "solvate" as used herein means a compound, or a salt of a compound, wherein molecules of a suitable solvent are incorporated in the crystal lattice.

General Techniques

Unless otherwise defined herein, scientific and technical terms used in connection with the present disclosure shall have the meanings that are commonly understood by those of ordinary skill in the art. Generally, nomenclatures used in connection with, and techniques of, cell and tissue culture, molecular biology, immunology, microbiology, genetics and protein and nucleic acid chemistry and hybridization described herein are those well-known and commonly used in the art.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, N Y (2001); Ausubel et al., Current Protocols in Molecular Biology, John Wiley & Sons, N Y (2002); Harlow and Lane Using Antibodies: A Laboratory Manual, Cold Spring Harbor Laboratory Press, Cold Spring Harbor, N Y (1998); Coligan et al., Short Protocols in Protein Science, John Wiley & Sons, N Y (2003); Short Protocols in Molecular Biology (Wiley and Sons, 1999); and Immunobiology (C. A. Janeway and P. Travers, 1997).

G9a and/or GLP Methyltransferase Inhibitors

G9a and/or GLP methyltransferase inhibitors include compounds, compositions or formulations that decrease or inhibit the expression, abundance and/or activity of G9a and/or GLP methyltransferase enzymes. The G9a and/or GLP methyltransferase inhibitors may bind selectively to G9a and/or GLP methyltransferase. In embodiments of the disclosure, the G9a and/or GLP methyltransferase inhibitors selectively decrease or inhibit the histone H3 lysine 9 dimethylation (H3K9me2) reaction catalyzed by G9a and/or GLP methyltransferase.

In embodiments of the disclosure, the G9a and/or GLP methyltransferase inhibitors may be one or more compounds selected from the compounds A366, UNC0638 or UNC0642, a derivative thereof, a pharmaceutically acceptable salt and/or solvate thereof, and combinations thereof. As demonstrated by way of examples herein, A366, UNC0638 or UNC0642 maintain high in vitro and cellular potency, low cell toxicity, and excellent selectivity, but also display improved in vivo pharmacokinetic properties, making them suitable for therapeutic methods and uses. Each of A366, UNC0638 and UNC0642 is commercially available.

A366 is
5-Methoxy-6'-[3-(1-pyrrolidinyl)propoxy]spiro[cyclobutane-1,3'-[3H]indol]-2'-amine, as represented by the formula:

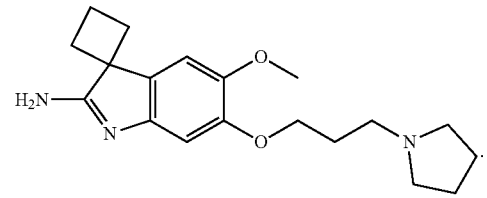 [SMILES: COc1cc2c(cc1OCCCN1CCCC1)N=C(N)C21CCC1]

UNC0638 is
2-Cyclohexyl-N-(1-isopropylpiperidin-4-yl)-6-methoxy-7-(3-(pyrrolidin-1-yl)propoxy)quinazolin-4-amine,
as represented by the formula:

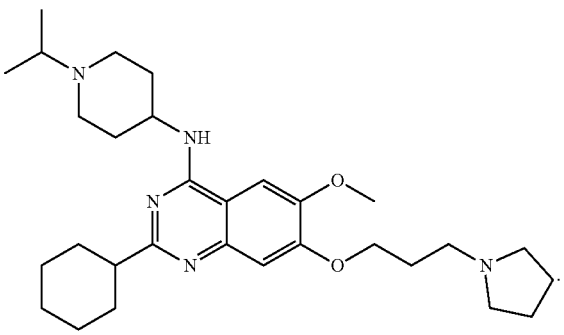 [SMILES: COc1cc2c(NC3CCN(C(C)C)CC3)nc(C3CCCCC3)nc2cc1OCCCN1CCCC1]

UNC0642 is
2-(4,4-Difluoropiperidin-1-yl)-6-methoxy-N-[1-(propan-2-yl)piperidin-4-yl]-7-(3-(pyrrolidin-1-yl) propoxy]quinazolin-4-amine,
as represented by the formula:

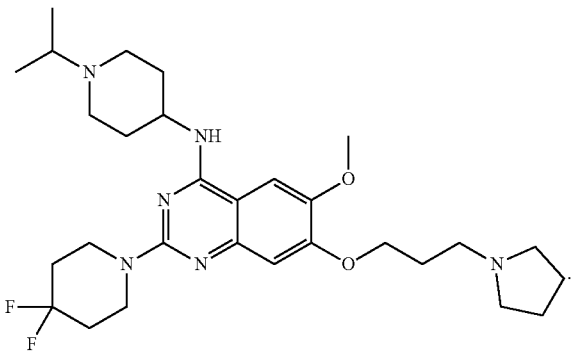 [SMILES: COc1cc2c(NC3CCN(C(C)C)CC3)nc(N3CCC(F)(F)CC3)nc2cc1OCCCN1CCCC1]

Therapeutic Methods

The methods disclosed herein comprise administering a therapeutically effective amount, or effective amount, of a G9a and/or GLP methyltransferase inhibitor to a subject in need of treatment. In embodiments of the disclosure, the G9a and/or GLP methyltransferase inhibitor may be one or more compounds selected from A366, UNC0638 or UNC0642, a derivative thereof, a pharmaceutically acceptable salt and or solvate thereof, and combinations thereof. In an embodiment, the method comprises administering one of the above therapies to the subject. In an embodiment, the method comprises administering two of the above therapies to the subject. In an embodiment, the method comprises administering all three of the above therapies to the subject. When used in combination, the therapies can be administered concurrently or sequentially in any order. The therapies may be combined in a single pharmaceutical composition, or formulated in separate pharmaceutical formulations.

The subject who may benefit from the therapeutic methods disclosed herein may have a vascular leakage-associated disease or disorder, such as an infection and/or inflammation. The subject who may benefit from the therapeutic methods disclosed herein may have, for example, sepsis, acute respiratory distress syndrome (ARDS), influenza virus infection, Dengue virus infection, Ebola virus infection, SARS virus infection, MERS-CoV virus infection, 2019-nCoV virus infection, pancreatitis, trauma, or post-transplant ischemia-reperfusion injury. In a preferred embodiment, the subject who may benefit from the therapeutic methods disclosed herein has sepsis.

Routes of administration of the G9a and/or GLP methyltransferase inhibitor to the subject include, but are not limited to, parenteral, topical, transdermal, parenteral, gastrointestinal, transbronchial and transalveolar. Parenteral routes of administration include but are not limited to electrical or direct injection such as direct injection into a central venous line, intravenous, intramuscular, intraperitoneal, intrathecal or subcutaneous injection. Topical administration is accomplished via a topically applied cream, gel, rinse, etc. containing an oligonucleotide conjugate. Transdermal administration is accomplished by application of a cream, rinse, gel, etc. capable of allowing the G9a and/or GLP methyltransferase inhibitor to penetrate the skin and enter the blood stream. Gastrointestinal routes of administration include but are not limited to ingestion and rectal administration. Transbronchial and transalveolar routes of administration include but are not limited to inhalation, either via the mouth or intranasally. Administration may also be done directly to the site of the infection or inflammation.

EXAMPLES

The disclosure is further described in detail by reference to the following examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Example 1: Materials and Methods

Zebrafish Strains and Care

Adult and embryonic zebrafish were raised, cared for and staged using standard laboratory procedures (Avdesh et al. 2012; Nusslein-Volhard & Dahm, 2002; Westerfield 2000; Kimmel et al. 1995). Briefly, zebrafish were raised on 14 h/10 h light/dark cycle at 28.5±0.5° C. Embryos were obtained via natural mating and cultured in egg water. All experiments in this study were carried out according to the ethical guidelines established by the St. Michael's Hospital (SMH) Animal Committee. Embryos older than 24 hours post-fertilization (hpf) were treated with 200 μM 1-phenyl-2-thiourea (PTU) to block pigmentation.

Zebrafish Sepsis Model

An LPS induced zebrafish sepsis model which mimics the hallmarks of human sepsis was developed (Philip et al., 2017). Zebrafish show varied susceptibility and responsiveness to LPS from different bacterial strains. Exposure of zebrafish larvae at 3 days post-fertilization (dpf) to two types of LPS (LPS from *Escherichia coli* 0111:B4 (Sigma) at 100 μg/ml for 5-6 hrs; or LPS from *Salmonella* at 27 μg/ml for 24 hrs) were both effective in inducing tail fin swelling, increased ROS production, increased vascular leakage and increased mortality.

Survival Curve and EC50

Survival analyses for zebrafish (wildtype) exposed to various concentrations of LPS (*Escherichia coli* 0111:B4; Sigma) was performed. 3 dpf larvae were exposed to LPS by immersion technique. Larvae were treated with 10, 25, 50, 125, 250, 500, 1000, 2500, 5000 or 10000 nM UNC0642 along with 100 μg/ml LPS (LPS was dissolved in eggwater), by static immersion at 28.5° C. for 24 h in a total volume of 2 mL per treatment. Control larvae were exposed to egg water. Survival numbers were recorded and EC50s calculated.

Measuring Vascular Leakage 3 dpf Tg (flk1:GFP; gata-1:Dsred) double transgenic larvae were exposed to Vehicle, LPS (100 μg/ml) or LPS+1 μM UNC0642 by static immersion for 6 h at 28.5° C. to induce endothe-lial dysfunction and the resulting leakage of red blood cells. The larvae were then imaged using a Leica fluorescence microscope (Leica Microsystems, Wetzlar, Germany). Red blood cells that leaked out into the tailfin region were quantified.

Measuring ROS Production

ROS production was visualised using 2', 7'-dichlorodihydrofluorescein diacetate (DCFH-DA; Sigma-Aldrich), a ROS indicator. Wildtype zebrafish were exposed to Vehicle, LPS (100 μg/ml) or LPS+1 μM UNC0642 by static immersion for 5 h at 28.5° C. and then incubated along with 100

µM DCFH-DA for 1 h at 28.5° C. in the dark, and washed three times (5 min each) with embryo water. DCFH-DA diffuses into cells and is deacetylated by cellular esterases to non-fluorescent 2', 7'-Dichlorodihydrofluorescin (DCFH), which is rapidly oxidized to highly fluorescent 2', 7'-Dichlorofluorescein (DCF) by ROS. The fluorescence intensity is propor-tional to the ROS levels within the cell cytosol. Photographs were acquired using a Leica DFC 300-FX camera and a Leica fluorescence microscope, and were processed with Fiji analysis software. Corrected total fluorescence (CTF) was calculated using the following formula:

$$CTF = \text{Integrated density} - (\text{Area of selected cell} \times \text{Mean fluorescence of background readings})$$

H3K9me2 Immunofluorescence Analysis 3 dpf Tg eGFP) larvae were exposed to Vehicle, LPS (100 µg/ml) or LPS+1 µM UNC0642 by static immersion for 5 h at 28.5° C. Embryos were fixed overnight at 4° C. in 2% PFA in PBST (PBS+0.1% Tween 20). Embryos were then washed 4×5 min in PBST at room temperature (RT) and permeabilized for 30 min at RT in PBST+0.5% TritonX-100. Embryos were then blocked in PBST+0.1% TritonX-100+ 10% NGS+1% BSA for 2 h at RT. Embryos were incubated with primary antibodies (Mouse monoclonal (mAbcam 1220) to Histone H3 (di-methyl K9) in blocking solution (1:200) overnight at 4° C. Embryos were then washed 6×20 min in PBST at RT and then incubated with the secondary antibody (Goat anti-mouse IgG Alexa fluor 647; 1:1000) in blocking solution for 2 h at RT. Embryos were finally washed 3×10 min in PBST at RT. Images were taken with a Zeiss Confocal Microscope.

G9a Morpholino Experiments

To assess if G9a inhibition in zebrafish larvae will offer protection against LPS induced sepsis, morpholinos were used to knockdown G9a methyltransferase. Subsequent to G9a knockdown, larvae were exposed to 100 µg/ml LPS at 3 dpf and survival numbers were determined. To knockdown G9a gene expression, a splice site-blocking morpholino oligonucleotide (G9a-sp MO) was used, in comparison to a standard control MO (ctrl MO). The following MO sequences were used:

```
G9a-sp MO:
                              (SEQ ID NO: 1)
5'-GACACACACTGACCTGCAGATGATC-3';
and ctrl MO:
                              (SEQ ID NO: 2)
5'-CCTCTTACCTCAGTTACAATTTATA-3'.
```

MOs were designed by Gene Tools, LLC. MOs were injected into 1-cell stage zebrafish embryos (2 nl of 100 µM MO solution/embryo).

Comparison of UNC0642 and A366

3 dpf larvae were exposed to LPS by immersion technique. Larvae were treated with 0.05, 0.1, 0.2, 0.5, 1, 10, 100, 1000 or 10000 nM UNC0642/A366 along with 27 µg/ml LPS (LPS was dissolved in eggwater), by static immersion at 28.5° C. for 24 h in a total volume of 2 mL per treatment. Control larvae were exposed to egg water. Survival numbers were recorded and EC50s calculated. The percentage (%) of embryos showing vascular leakage was also recorded and 1050s calculated.

G9a Inhibitor In Vitro Screening Assay

The commercially available Histone H3 (K9) Methyltransferase Activity Quantification Assay Kit (ab113453) was used for this assay and a modified protocol was adopted. Briefly, the histone substrate is stably captured on the strip wells. Uninhibited G9a methyltransferase (active human EHMT2/G9a protein fragment (ab80323)) will transfer a methyl group to histone H3 substrate from Adomet to methylate the substrate at lysine 9. The methylated histone H3K9 can be recognized with a high-affinity antibody. The ratio or amount of methylated H3K9, which is directly proportional to enzyme activity, can be quantified through HRP-conjugated secondary antibody color development system. In the presence of inhibitors of G9a methyltransferase, this reaction will be inhibited. Assay steps are given below:

(a) Determine the number of strip wells required and put them in the plate frame.
(b) Add 24 µL of Histone Assay Buffer, 1.5 µL of the diluted Adomet, and 2 µL of Biotinylated Substrate to each strip well.
(c) To the uninhibited enzyme wells, add 3 µL of G9a protein fragment.
(d) To the inhibitor wells, add 3 µL of G9a protein fragment along with 3 µL of inhibitors at different concentrations (25 ng, 250 ng and 2500 ng) and reduce Histone Assay Buffer volume to 21 µL.
(e) For the blank, add 3 µL of Histone Assay Buffer instead of G9a protein fragment.
(f) For the standard curve, add 3 µL of Histone Assay Buffer instead of G9a protein fragment, and add 2 µL of HMT Standard at different concentrations (e.g. 0.1-5 ng/µL) instead of Biotinylated Substrate.
(g) Mix and cover the strip wells with Parafilm and incubate at 37° C. for 60-90 minutes.
(h) Aspirate and wash each well with 150 µL of 1× Wash Buffer three times.
(i) Add 50 µL of diluted Capture Antibody to each strip well and incubate at room temperature for 60 minutes on an orbital shaker (50-100 rpm).
(j) Aspirate and wash each well with 150 µL of diluted 1× Wash Buffer five times.
(k) Add 50 µL of the diluted Detection Antibody to each strip well and incubate at room temperature for 30 minutes.
(l) Aspirate and wash each well with 150 µL of diluted 1× Wash Buffer five times.
(m) Add 100 µL of Developing Solution into the wells and incubate at room temperature for 2-10 minutes away from light. Monitor the color development in the sample and standard wells (blue).
(n) Add 50 µL of Stop Solution to each well to stop enzyme reaction when the color in the standard wells containing the higher concentrations of standard control turns medium blue. The color should change to yellow and absorbance can be read on a microplate reader at 450 nm within 2-15 minutes.

G9a activity or inhibition was calculated as follows: plot OD value versus amount of G9a Standard and determine the slope. Calculate G9a activity using the following:

$$\text{Activity (ng/h/mg)} = [(\text{Sample OD} - \text{Blank OD})/\text{G9a amount (µg)} \times \text{hour} \times \text{slope}] \ast 1000$$

Testing UNC0642 in a Mouse Cecal Ligation and Puncture (CLP) Model of Sepsis

The CLP model is a well established clinically relevant model for human sepsis (Smeding et al., 2012; Amatullah et al., 2016). Male 8-12 week old C57/B16 mice (Jackson lab) were randomized to CLP or sham surgeries. In anesthetised mice, the cecum was exteriorized, ligated, and perforated. Control animals were exposed to sham surgery, in which the cecum was manipulated, but not ligated or punctured. After surgery, animals received daily fluid resuscitation (subcutaneous (s.c.) 50 ml/kg saline), antibiotic (intraperitoneal (i.p.) imipenem 25 mg/kg) and pain management (s.c. buprenorphine 0.2 mg/kg). Experiments were divided into 2 groups: (1) to assess 7-day survival, and (2) to identify a mechanism of action of a G9a inhibitor in vivo. All experimental mice were randomized and investigators were blinded to group assignment.

Assessment of protective effects of UNC0642 on sepsis-induced vascular leakage: lung injury score and loss of alveolar-capillary membrane integrity with increased albumin and IgM exudation into bronchoalveolar lavage fluid (BALF) was assessed at 24 hrs post treatment.

Effects of UNC0642 on Barrier Function and Integrity in Cultured Human Endothelial Cells Cultured endothelial cells are used to model the microvascular endothelium, because of the feasibility of performing complex molecular or pharmacological experiments to study cellular signalling pathways related to barrier function and integrity. In addition, the lung is the organ most often affected by sepsis induced-MODS. To determine the functional significance of G9a inhibition in human cells, solute permeability and electrical resistance across a confluent human pulmonary microvascular endothelial cell (HPMEC) monolayer was assessed. For both experiments HPMECs were seeded on 0.4 µm-pore polyester transwells (Costar) coated with Attachment Factor (Invitrogen), grown to confluency, and then transfected with either UNC0462 or vehicle control.

Assessment of endothelial stability and paracellular permeability: The medium in both the top and bottom compartment was replaced with Dulbecco's Phosphate-Buffered Saline (DPBS), and the cells were exposed to 2 mg/ml FITC-labeled dextran (70 kDa) in the absence or presence of recombinant TNFα (a pro-inflammatory cytokine markedly upregulated in sepsis) or LPS. FITC fluorescence was be measured at different time intervals in samples taken from the bottom compartment as a measure of paracellular dextran leak.

Effects of UNC0642 on ROS Production in Beas2b Human Airway Epithelial Cells

Beas2b human airway epithelial cells were grown to 70% confluency. Cells were treated with TNFα (10 ng/mL) or an equal volume of nuclease-free water in the presence of 0, 0.25, 2.5, or 25 nM of UNC0642. Cell lysates were collected in 1×PBS after 24 hr and freeze-thawed twice to lyse the cells completely. In vitro ROS was measured using OxiSelect In Vitro ROS/RNS Assay Kit with DCF standard. ROS (nM) was calculated from the standard curve and values were normalized by total amount of protein (as measured by Bradford assay). Values are expressed as mean+/-SEM (average of two experimental replicates).

Western Blots and Real Time PCR

HPMECs were grown to 90% confluency, exposed to LPS (1 ug/ml)+/-UNC0642 (2.5 nM) for 24 hours. Western Blot analysis showed decreased H3K9me2 in cells treated with UNC0642. Relative changes in abundance of mRNA for the Tight Junction protein Occludin and the antioxidant gene NAD(P)H Quinone Dehydrogenase 1 gene (Nqo-1) compared to β-actin were measured by real time PCR.

Effects of UNC0638 on Neutrophils from Septic Patients

Circulating PMN from patients with sepsis (N=5) were incubated with increasing concentrations of the G9a and/or GLP inhibitor, UNC0638. Apoptosis was quantified after 24 hours by flow cytometry as the uptake of propidium iodide in permeabilized cells.

Example 2: Development of a Zebrafish Model of Sepsis

With a sequenced genome, the zebrafish has recently emerged as a robust vertebrate model for disease modeling because of its physiological similarity to humans, high fecundity, low costs, transparency and relative ease of embryonic manipulation (Lieschke and Currie, 2007). In drug research, the zebrafish has also emerged as a key model organism for high throughput in vivo drug screening. In contrast to traditional target-based screening in vitro, the zebrafish provides a whole vertebrate system for phenotype-based screening. It combines the biological complexity of in vivo models with the ability for high-throughput screening and quick assessment of potential toxicity early on in the drug development process (Miscevic, Rotstein and Wen, 2012). Due to the nature of the in vivo screen and initial toxicity assessment of the compounds on developing embryos, lead compounds identified from a phenotype-based in vivo screen targeting entire disease pathways should have higher success rates than traditional single target-based in vitro screens.

To this end, a zebrafish sepsis model was developed. This model displays all the major hallmarks of human sepsis, including edema and tissue/organ damage, increased vascular permeability and vascular leakage accompanied by altered expression of cellular junction proteins, increased cytokine expression, immune cell activation and ROS production, reduced circulation and increased platelet aggregation (Philip et al., 2017). This model was further validated for suitability for phenotype-based drug screening using three primary readouts: mortality, vascular leakage and ROS production (Philip et al., 2017).

Example 3: Therapeutic Effects of UNC0642 in a Zebrafish Model of Sepsis

High-throughput screening in the zebrafish model of sepsis identified UNC0642, an epigenetic regulator of histone methylation with potent anti-sepsis properties.

UNC0642 improved the survival of septic zebrafish larvae in a dose dependent manner with an EC50 of 788.6 nM. UNC0642 also significantly reduced LPS-induced vascular leakage and tailfin edema. While LPS-treated larvae showed a significantly higher number of leaked out red blood cells at the tail fin region (measured by using transgenic zebrafish larvae having fluorescently labelled red blood cells), this pathophysiological manifestation of vascular leakage was mitigated in larvae which received UNC0642 treatment. Another pathophysiological hallmark of sepsis is the excessive generation of ROS, which inevitably leads to oxidative stress in the microvasculature. It was found that UNC0642 significantly reduced LPS-induced ROS production by 40%. This effect was most pronounced at the tail fin region which corresponded with the observed tail and tissue damage.

Example 4: Therapeutic Effects of Intravenous UNC0642 Infusion on CLP-Induced Mortality and Vascular Leakage in Mice Intravenous infusion of 1 mg/kg of UNC0642 reduced CLP-induced absolute mortality by close to 50%. This therapeutic effect was associated with reduced protein exudation into the alveolar space, as measured by total alveolar protein in the BALF.

Example 5: Therapeutic Effects of UNC0642 Infusion on Inflammation-Induced Endothelial Barrier Dysfunction in HPMECs and Increased ROS Production in Beas2b Cells HPMECs were used to study endothelial barrier function due to the critical importance of pulmonary vascular barrier function in sepsis, and LPS was applied to HPMECs to mimic inflammatory pulmonary conditions in vitro. The permeability of the endothelial monolayer was tested by measuring the influx of FITC-conjugated dextran across cells. LPS was found to induce endothelial barrier dysfunction, as represented by increased dextran leakage. UNC0642 was able to significantly mitigate these changes. TNFα-induced increased ROS production in beas2b cells and this effect was also significantly lowered in the presence of UNC0642.

Example 6: Therapeutic Effects of UNC0642 are Partially Mediated Through the Downregulation of G9a Methyltransferase Activity Using an in vitro histone methyltransferase assay, it was found that UNC0642 inhibits G9a methyltransferase activity in a dose dependent manner. These biochemical results parallel our in vivo zebrafish findings that UNC0642 rescues LPS induced increased H3K9me observed exclusively in venous endothelial cell nuclei. Western Blot also shows increased H3K9me in HPMECs treated with LPS and a reduction in this H3K9me2 in the presence of UNC0642. This was also paralleled by relative changes in abundance of mRNA for the Tight Junction protein Occludin and the antioxidant gene NAD(P)H Quinone Dehydrogenase 1 gene (Nqo-1) compared to β-actin. Moreover, morpholino based knockdown/downregulation of G9a methyltransferase in zebrafish larvae resulted in improved survival (>4 fold) upon subsequent LPS exposure. A comparison of UNC0642 and A366, another G9a methyl transferase inhibitor, showed and validated that G9a methyltransferase activity is critical to sepsis. Both UNC0642 and A366 were able to rescue sepsis-associated vascular leakage and mortality in zebrafish larvae.

Example 7: Therapeutic Effects of G9a and/or GLP Methyltransferase Inhibitors on the Delayed Apoptosis Seen in Septic Neutrophils Isolated from Patients with Sepsis While circulating neutrophils have a short half-life of 7-12 hrs in vivo under normal conditions, neutrophils in septic patients have an increased life span owing to their ability to resist apoptosis. Neutrophils from septic patients also exert a dramatic compromise of endothelial barrier integrity, leading to vascular leakage.

Treatment of neutrophils isolated from septic patients with a G9a and/or GLP methyltransferase inhibitor was found to successfully induce apoptosis in these cells.

Example 8: Comparison of Toxicity Effects of UNC0642 vs A366 in Zebrafish Larvae Another G9a and/or GLP methyltransferase inhibitor A366 was tested zebrafish sepsis model. A366 is a potent inhibitor of G9a (IC50: 3.3 nM) with greater than 1000-fold selectivity over 21 other methyltransferases. Furthermore, A366 has a low molecular weight of 329 daltons suggesting a suitable binding efficiency index (BEI).

Figure 7:
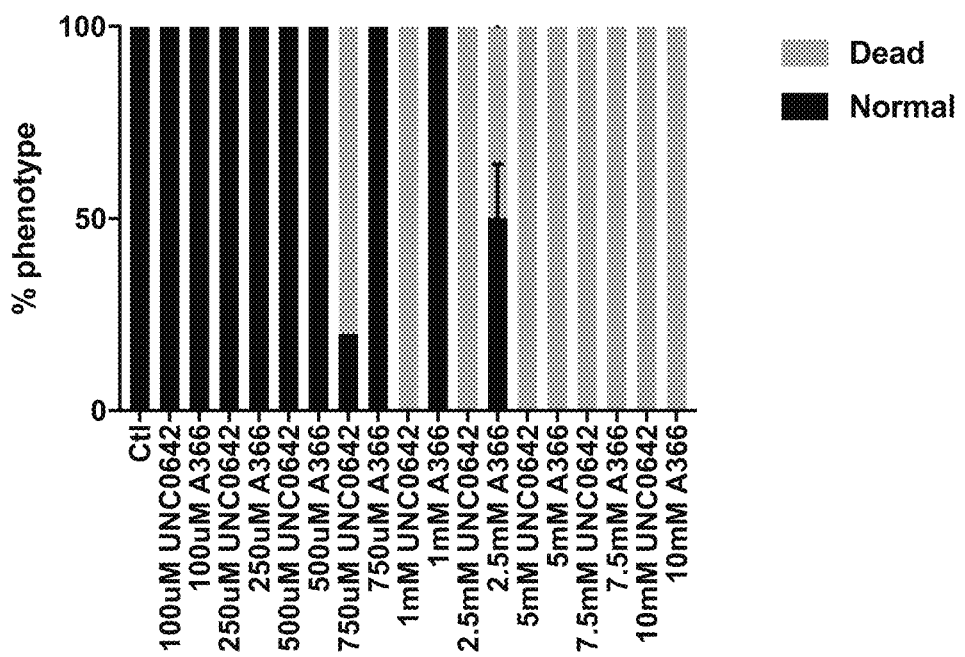
FIG. 7 shows dose dependent toxicity effects of A366 and UNC0642.

Zebrafish larvae at 3 dpf were exposed to varying concentrations of UNC0642 or A366 (100 µM, 250 µM, 500 µM, 750 µM, 1 mM, 2.5 mM, 5 mM, 7.5 mM, 10 mM) and observed daily for 72 hours post incubation. Parameters of developmental toxicity (organ size and shape), cardiac toxicity (cardiac edema and heart rate), neuromuscular toxicity (touch response) and finally death were investigated. See FIG. 7 for mortality of larvae with various doses of A366 and UNC0642. A366 is non-toxic to zebrafish embryos below about 2.5 mM.

Example 9: Quantitative RT-PCR

Measuring Expression of Cytokines and Cellular Junction Proteins

Figure 8:
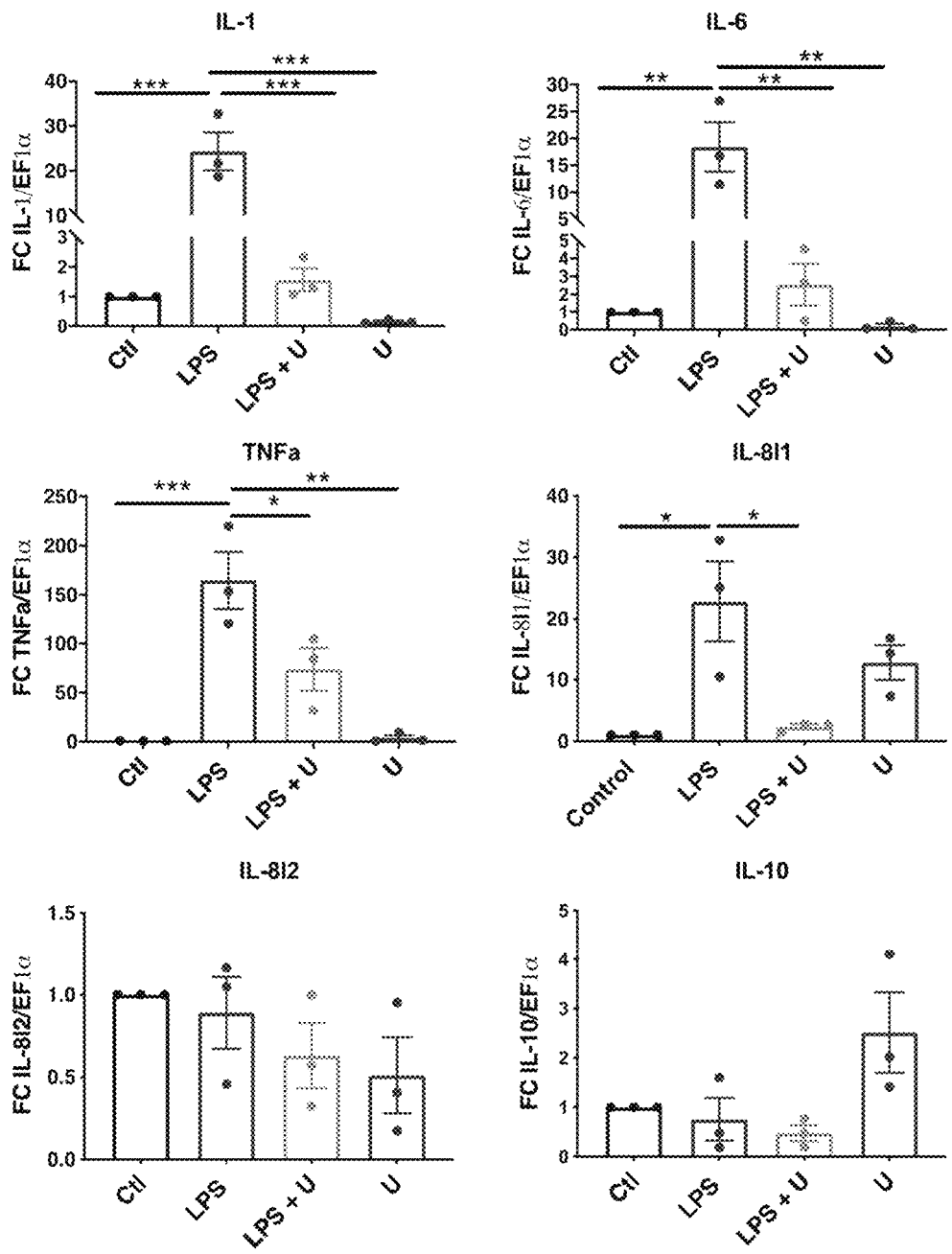
FIG. 8 shows the fold-change in transcript levels of pro-inflammatory cytokines IL-1, IL-6, TNFα and IL-811 in LPS treated larvae with or without UNC0642 measured by quantitative RT-PCR.
Figure 9:
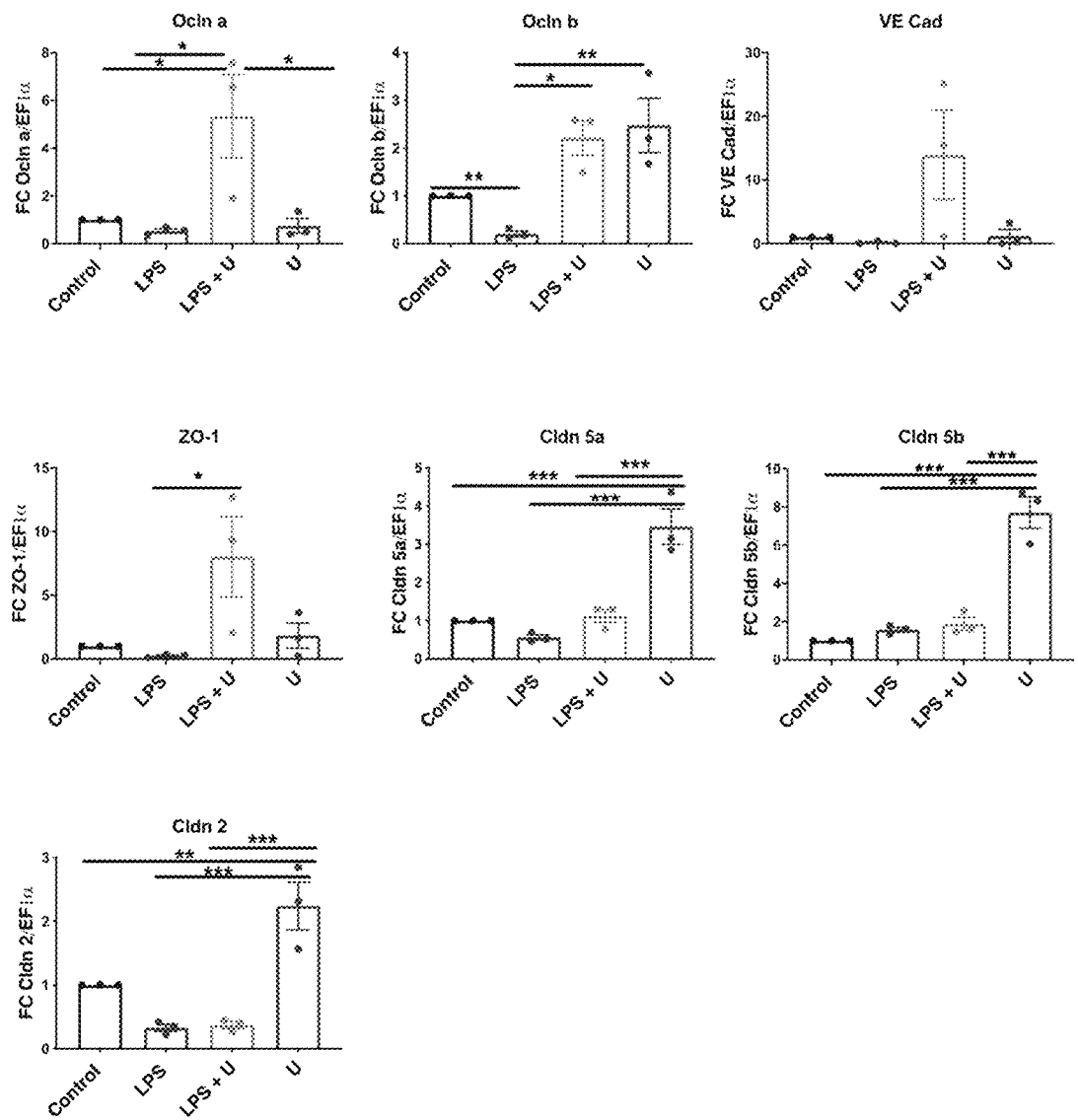
FIG. 9 shows the fold-change in transcript levels of cellular junction proteins such as occludin a, occludin b and ZO-1 in LPS treated larvae with or without UNC0642 measured by quantitative RT-PCR.

Quantitative reverse transcription polymerase chain reaction (RT-PCR) was used to assess relative expression of cytokines (an average of 3 trials, each trial with a pool of 20 larvae/treatment) and cellular junction proteins (an average of 3 trials, each trial with a pool of 20 larvae/treatment), using elongation factor 1 a (EF1a) as the housekeeping gene control. Results are presented in FIGS. 8 and 9. UNC0642 significantly mitigates LPS induced increases in the transcript levels of pro-inflammatory cytokines namely IL-1, IL-6, TNFα and IL811 in the zebrafish sepsis model. UNC0642 reverses LPS induced reduction in the transcript levels of cellular junction proteins, namely occludin a, occludin b and ZO-1. UNC0642 also upregulates cellular junction protein transcript levels of occludin b, claudin 5a, claudin 5b and claudin 2, potentially improving vascular stability.

RNA extraction and cDNA synthesis. Wildtype zebrafish larvae (3 dpf) were exposed to Vehicle, LPS (27 µg/ml; LPS from *Salmonella*) or LPS+1 µM UNC0642 by static immersion for 24 h. Total RNA was extracted from these larvae (pool of 20 larvae/treatment) using the RNeasy extraction kit (Qiagen™, Mississauga, Ontario, Canada) and treated with DNase. The concentration of total RNA was determined spectrophotometrically at 260/280 nm using a NanoDrop™ spectrophotometer. First-strand cDNA was synthesized from 1 µg of total RNA using the Superscript II reverse transcriptase kit (Invitrogen) according to the manufacturer's instructions.

PCR conditions. The genes of interest and the primer pairs used are given in Table 1. Amplification of cDNA was achieved using a two-step RT-PCR protocol. Amplification of cDNA was achieved with an initial denaturation at 95° C. for 10 min followed by 40 cycles of denaturation (95° C. for 15 s), annealing (60° C. for 1 min). PCR was carried out in a 10 µl total volume and included 1×PCR buffer, 1.25 mM $MgCl_2$, 0.25 mM dNTP, 1 U Taq polymerase, 0.5 µM forward and reverse primers and 1 µl cDNA. The primers are not listed, since suitable primers will be readily apparent to the skilled person.

Example 10: Immunostaining of the Cellular Junction Protein VE Cadherin in HUVEC Cells HUVEC cells were seeded onto Lab-Tek II Chamber slide system at $1\times10^6$ cells/ml and grown to confluency. At 80-95% confluency they were treated with either the vehicle, LPS (1 µg/ml), LPS (1 µg/ml)+UNC0642 (2.5 nM) or UNC0642 (2.5 nM) for 24 hours. Then the following steps for immunostaining were performed
1. Fixed the cells in 4% formaldehyde in warm PBS for 20 minutes at room temperature
2. Aspirated the fixative 3. Washed 3 times in PBS, 5 minutes each
4. Blocked in blocking buffer for 2 hours at room temperature
5. Aspirated the blocking buffer
6. Added primary antibody VE cadherin (monoclonal VE Cad; cell signalling 2500S) at a dilution of 1:200 and incubated overnight at 4° C.
7. Washed 3 times in PBS, 10 minutes each
8. Added secondary antibody (goat anti-rabbit IgG Alexa Fluor 568; 1:1000 and Alexa Fluor 488 phalloidin; 1:1,000) and incubated for 2 hours at room temperature.
9. Washed the cells 3 times in PBS, 10 minutes each at room temperature and mounted with a cover slip in 4',6-diamidino-2-phenylindole (DAPI) Vectashield.

Figure 10:
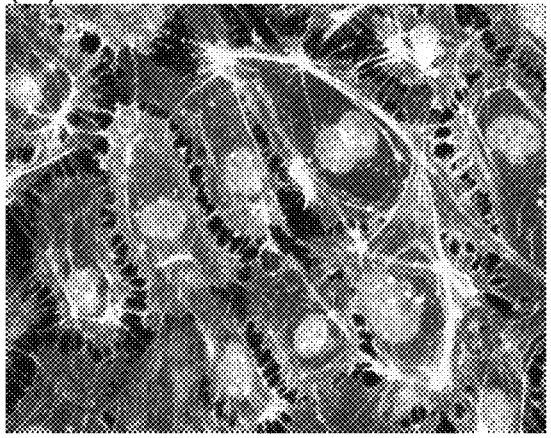
FIG. 10 shows confocal microscopy images of HUVEC cells treated with (A) control, (B) LPS, (C) LPS and UNC0642, or (D) UNC00642 alone, immunostained for cellular junction protein VE cadherin.
Figure 10:
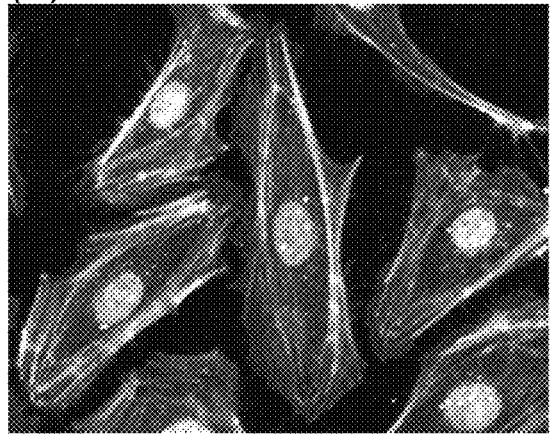
Figure 10:
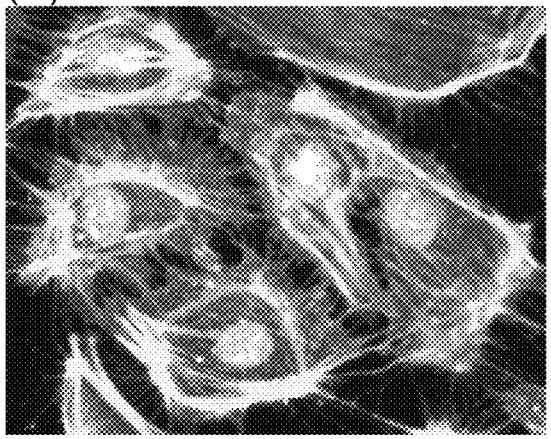
Figure 10:
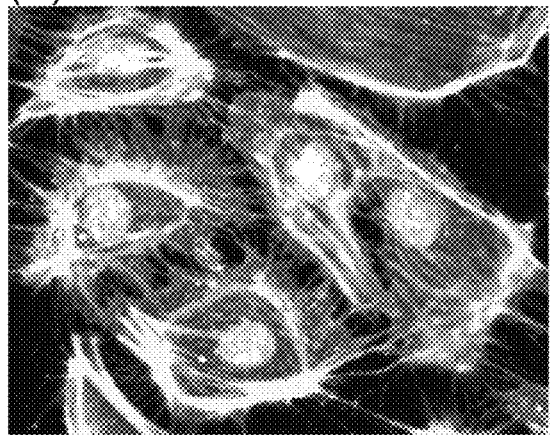

Images were taken with a Zeiss™ confocal microscope. While LPS causes a decrease in the level and patterning of VE cadherin, this effect can be partially rescued in the presence of UNC0642. (FIG. 10)

Example 11: Endothelial Permeability Assay and TEER Assay Using HUVEC Cells

To determine the functional significance of G9a inhibition in human cells, solute permeability and electrical resistance across a confluent HUVEC monolayer was assessed. For both experiments, HUVEC were seeded at $1\times10^6$ cells/ml on Matrigel™ coated 3-μm pore size transwell inserts in 24-well plates from BD Discovery Labware™ (catalog number 354575) and grown to confluency. The cells were then treated with either the vehicle, LPS (1 μg/ml) or LPS (1 μg/ml)+UNC0642 (2.5 nM).

Figure 11:
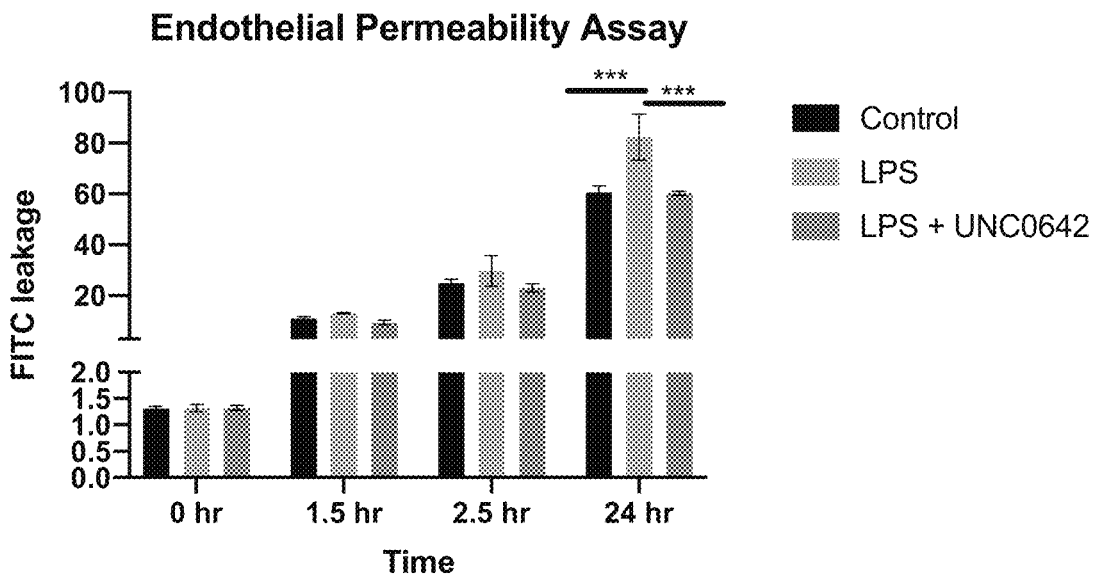
FIG. 11 shows in panel A the results of a FITC dextran leakage assay in LPS-treated HUVEC cells treated with or without UNC0642. In panel B, the results of an endothelial transendothelial electrical resistance (TEER) assay in LPS-treated HUVEC cells with or without UNC0642.
Figure 11:
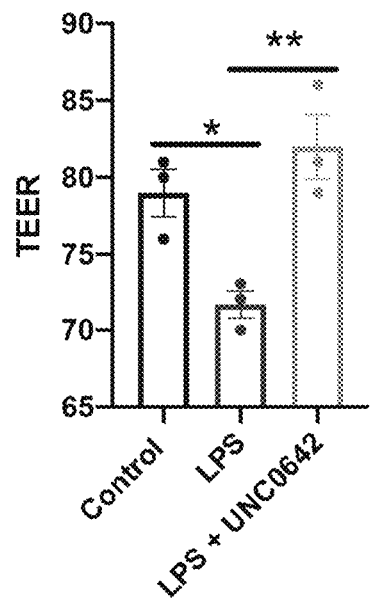

Assessment of Paracellular Permeability: Dextran sulfate-FITC (3 kD, Invitrogen™ Molecular Probes catalog number D-3306) was added to the lower chamber to a final concentration of 10 μg/ml. Simultaneously, the different treatment conditions mentioned above were added to the lower chamber. FITC fluorescence was measured at different time intervals (0 h, 1.5 h, 2.5 h, 24 h) in samples taken from the top chamber as a measure of paracellular dextran leak. In human umbilical vein endothelial cells (HUVECs) cultured on transwell plates, UNC0642 protects against LPS induced vessel permeability in a FITC dextran leakage assay. (FIG. 11, Panel A)

Assessment of trans-endothelial electrical resistance (TEER): At 24 h post treatment, trans endothelial electrical resistance across the HUVEC monolayer was measured using the Endohm-12 (WPI, Florida). UNC0642 improves transendothelial electrical resistance (TEER) which is also an indicator of vessel integrity and stability. (FIG. 11, Panel B)

Although the disclosure has been described with reference to certain specific embodiments, various modifications thereof will be apparent to those skilled in the art. Any examples provided herein are included solely for the purpose of illustrating the disclosure and are not intended to limit the disclosure in any way. Any drawings provided herein are solely for the purpose of illustrating various aspects of the disclosure and are not intended to be drawn to scale or to limit the disclosure in any way. The scope of the claims appended hereto should not be limited by the preferred embodiments set forth in the above description, but should be given the broadest interpretation consistent with the present specification as a whole. All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS OF DOCUMENTS REFERENCED

1. Alexandraki, I. and Palacio, C. (2010) 'Gram-negative versus Gram-positive bacteremia: what is more alarmin (g)?', Critical Care, 14(3), p. 161. doi: 10.1186/cc9013.
2. Avdesh, A. et al. (2012) 'Regular care and maintenance of a zebrafish (Danio rerio) laboratory: an introduction.', Journal of visualized experiments: JoVE, (69), p. e4196. doi: 10.3791/4196.
3. Cinel, I. and Opal, S. M. (2009) 'Molecular biology of inflammation and sepsis: a primer.', Critical care medicine, 37(1), pp. 291-304. doi: 10.1097/CCM.0b013e31819267fb.
4. Cole, J. et al. (2016) 'The therapeutic potential of epigenetic manipulation during infectious diseases.', Pharmacology & therapeutics. Elsevier, 167, pp. 85-99. doi: 10.1016/j.pharmthera.2016.07.013.
5. Foster, S. L., Hargreaves, D. C. and Medzhitov, R. (2007) 'Gene-specific control of inflammation by TLR-induced chromatin modifications', Nature, 447(7147), pp. 972-978. doi: 10.1038/nature05836.
6. Fox, E. D. et al. (2013) 'Neutrophils from critically ill septic patients mediate profound loss of endothelial barrier integrity.', Critical care (London, England). BioMed Central, 17(5), p. R226. doi: 10.1186/cc13049.
7. Gupta, S. et al. (2018) 'Heat-shock protein-90 prolongs septic neutrophil survival by protecting c-Src kinase and caspase-8 from proteasomal degradation', Journal of Leukocyte Biology, 103(5), pp. 933-944. doi: 10.1002/JLB.4A0816-354R.
8. Jiang, L. et al. (2016) 'Alteration of histone H3 lysine 9 dimethylation in peripheral white blood cells of septic patients with trauma and cancer.', Molecular medicine reports. Spandidos Publications, 14(6), pp. 5467-5474. doi: 10.3892/mmr.2016.5958.
9. Kimmel, C. B. et al. (1995) 'Stages of embryonic development of the zebrafish.', Developmental dynamics: an official publication of the American Association of Anatomists, 203(3), pp. 253-310. doi: 10.1002/aja.1002030302.
10. Lee, W. L., Ph, D. and Slutsky, A. S. (2010) 'clinical implications of basic research Sepsis and Endothelial Permeability', pp. 689-691.
11. Lieschke, G. J. and Currie, P. D. (2007) 'Animal models of human disease: zebrafish swim into view', Nature Reviews Genetics, 8(5), pp. 353-367. doi: 10.1038/nrg2091.
12. Marshall, J. C. (2014) 'Why have clinical trials in sepsis failed?', Trends in molecular medicine, 20(4), pp. 195-203. doi: 10.1016/j.molmed.2014.01.007.
13. Marshall, J. C. (2014) 'Why have clinical trials in sepsis failed?', Trends in Molecular Medicine. Elsevier Ltd, 20(4), pp. 195-203. doi: 10.1016/j.molmed.2014.01.007.
14. Medzhitov, R. (2008) 'Origin and physiological roles of inflammation.', Nature, 454(7203), pp. 428-435. doi: 10.1038/nature07201.
15. Miscevic, F., Rotstein, O. and Wen, X.-Y. (2012) 'Advances in zebrafish high content and high throughput technologies.', Combinatorial chemistry & high throughput screening, 15(7), pp. 515-21. Available at: http://www.ncbi.nlm.nih.gov/pubmed/22497524.

16. Nemzek, J. a., Hugunin, K. M. S. and Opp, M. R. (2008) 'Modeling sepsis in the laboratory: Merging sound science with animal well-being', *Comparative Medicine,* 58(2), pp. 120-128.
17. Nicodeme, E. et al. (2010) 'Suppression of inflammation by a synthetic histone mimic', *Nature,* 468(7327), pp. 1119-1123. doi: 10.1038/nature09589.
18. Philip, A. M. et al. (2017) 'Development of a Zebrafish Sepsis Model for High-Throughput Drug Discovery', *Molecular Medicine,* 23(1), p. 1. doi: 10.2119/molmed.2016.00188.
19. Shen, X.-F. et al. (no date) 'Neutrophil dysregulation during sepsis: an overview and update'. doi: 10.1111/jcmm.13112.

The invention claimed is:

1. A method of reducing vascular leakage in a subject in need thereof comprising administering an effective amount of a G9a and/or G9a-like protein (GLP) methyltransferase inhibitor.

2. The method of claim 1, wherein the vascular leakage is associated with infection and/or inflammation.

3. The method of claim 1, wherein the vascular leakage is associated with a disease, disorder or condition selected from sepsis, acute respiratory distress syndrome (ARDS), influenza virus infection, SARS virus infection, MERS-CoV virus infection, 2019-CoV virus infection, Dengue virus infection, Ebola virus infection, pancreatitis, trauma, post-transplant ischemia-reperfusion injury, and combinations thereof.

4. The method of claim 1, wherein the vascular leakage is associated with sepsis.

5. A method of treating a vascular leakage-associated disease, disorder or condition in a subject in need thereof comprising administering an effective amount of a G9a and/or G9a-like protein (GLP) methyltransferase inhibitor.

6. The method of claim 5, wherein the vascular leakage-associated disease, disorder or condition is an infection and/or inflammation.

7. The method of claim 6, wherein the vascular leakage-associated disease, disorder or condition is selected from sepsis, acute respiratory distress syndrome (ARDS), influenza virus infection, Dengue virus infection, Ebola virus infection, SARS virus infection, MERS-CoV virus infection, 2019-nCoV virus infection, pancreatitis, trauma, post-transplant ischemia-reperfusion injury, and a combination thereof.

8. The method of claim 5, wherein the vascular leakage-associated disease, disorder or condition is sepsis.

9. The method of claim 5, wherein the subject is a mammal.

10. The method of claim 9, wherein the mammal is a human.

11. The method of claim 5, wherein the G9a and/or G9a-like protein-(GLP) methyltransferase inhibitor is selected from

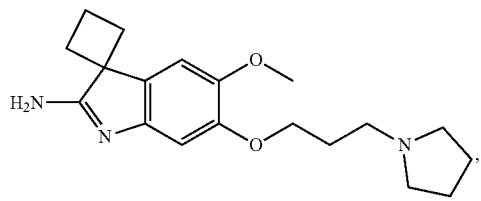

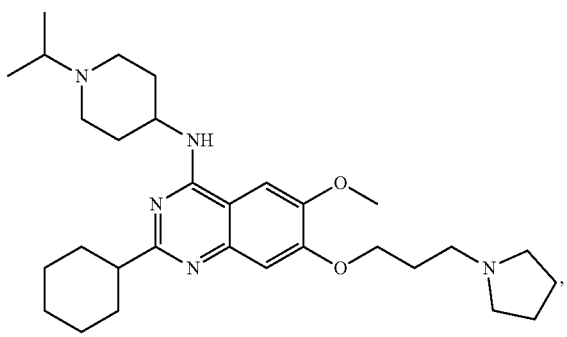

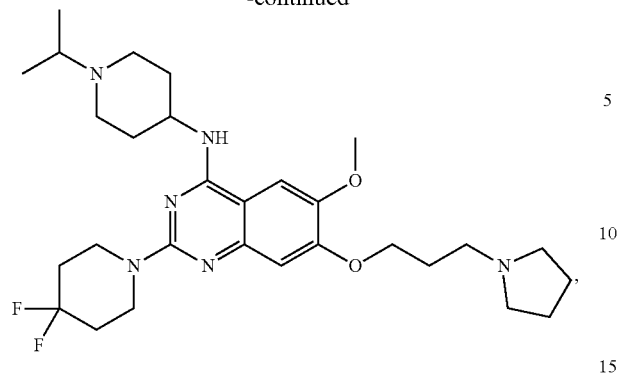
a pharmaceutically acceptable salt and/or solvate thereof, and a combination thereof.
* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic construct

<400> SEQUENCE: 1
gacacacact gacctgcaga tgatc                                         25

<210> SEQ ID NO 2
<211> LENGTH: 25
<212> TYPE: DNA
<213> ORGANISM: Artificial Sequence
<220> FEATURE:
<223> OTHER INFORMATION: Synthetic construct

<400> SEQUENCE: 2
cctcttacct cagttacaat ttata                                         25
```